(12) United States Patent
Guizzardi et al.

(10) Patent No.: US 9,820,863 B2
(45) Date of Patent: Nov. 21, 2017

(54) INTERVERTEBRAL SUPPORT

(76) Inventors: Giancarlo Guizzardi, Florence (IT);
Piero Petrini, Perugia (IT)

(*) Notice: Subject to any disclaimer, the term of this patent is extended or adjusted under 35 U.S.C. 154(b) by 776 days.

(21) Appl. No.: 13/819,022

(22) PCT Filed: Aug. 25, 2011

(86) PCT No.: PCT/IB2011/001947
§ 371 (c)(1),
(2), (4) Date: Jun. 17, 2013

(87) PCT Pub. No.: WO2012/028920
PCT Pub. Date: Mar. 8, 2012

(65) Prior Publication Data
US 2013/0274882 A1    Oct. 17, 2013

(30) Foreign Application Priority Data
Aug. 26, 2010 (IT) .................. PI2010A0100

(51) Int. Cl.
*A61F 2/44* (2006.01)
*A61F 2/46* (2006.01)
*A61F 2/30* (2006.01)

(52) U.S. Cl.
CPC ............ *A61F 2/442* (2013.01); *A61F 2/4425* (2013.01); *A61F 2/4611* (2013.01); *A61F 2/30771* (2013.01); *A61F 2002/30014* (2013.01); *A61F 2002/30018* (2013.01); *A61F 2002/30092* (2013.01); *A61F 2002/30331* (2013.01);
(Continued)

(58) Field of Classification Search
None
See application file for complete search history.

(56) References Cited

U.S. PATENT DOCUMENTS 6,113,637 A * 9/2000 Gill .................. A61F 2/4425
623/17.15
2004/0093083 A1   5/2004 Branch et al.
(Continued)

FOREIGN PATENT DOCUMENTS

EP    0 560 249 A1    9/1993
FR    2 543 821 A3    10/1984
(Continued)

OTHER PUBLICATIONS

International Search Report dated Mar. 30, 2012 for Application No. PCT/IB2011/001947.

*Primary Examiner* — Sameh Boles
(74) *Attorney, Agent, or Firm* — Ladas & Parry LLP

(57) ABSTRACT

An intervertebral support device to impose an anatomic distance between two adjacent vertebral bodies having a pair of vertebral support elements for introduction between the edge portions of the rear half of the vertebrae, at respective substantially symmetrical positions of the instantaneous rotation axis of the natural relative flexion-extension movement of the two adjacent vertebrae. The device assists stabilizing and/or restoring the correct position of the rotation axis, which characterizes the first stage of the degenerative breakdown, without significantly limiting the relative movement of the two vertebrae. The support elements have preferably a constraint means that constrains them to the edge portions of the vertebral bodies, in particular to resist the reaction force on the intervertebral disc.

24 Claims, 14 Drawing Sheets

(52) U.S. Cl.
CPC ............ *A61F 2002/30448* (2013.01); *A61F 2002/30462* (2013.01); *A61F 2002/30469* (2013.01); *A61F 2002/30517* (2013.01); *A61F 2002/30576* (2013.01); *A61F 2002/30578* (2013.01); *A61F 2002/30649* (2013.01); *A61F 2002/30772* (2013.01); *A61F 2002/30777* (2013.01); *A61F 2002/30841* (2013.01); *A61F 2002/30904* (2013.01); *A61F 2002/448* (2013.01); *A61F 2002/4415* (2013.01); *A61F 2002/4435* (2013.01); *A61F 2002/4495* (2013.01); *A61F 2310/00023* (2013.01); *A61F 2310/00071* (2013.01); *A61F 2310/00131* (2013.01)

(56) References Cited

U.S. PATENT DOCUMENTS

2005/0154464 A1* 7/2005 Humphreys .......... A61F 2/4405
623/17.16
2007/0050029 A1 3/2007 Carrasco

FOREIGN PATENT DOCUMENTS

| WO | 96/27345 | A2 | 9/1996 |
| WO | 01/41681 | A1 | 6/2001 |
| WO | 2004/012634 | A2 | 2/2004 |
| WO | 2005/081704 | A2 | 9/2005 |
| WO | 2007/048012 | A2 | 4/2007 |

* cited by examiner

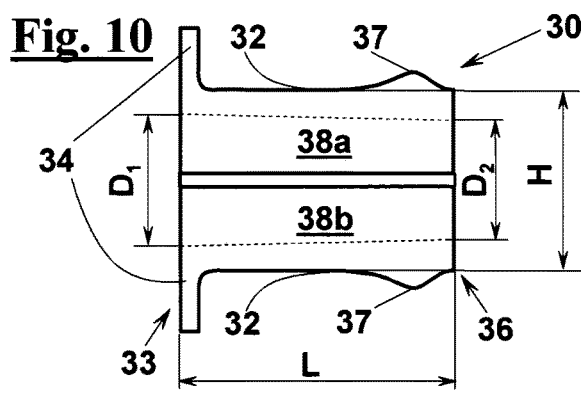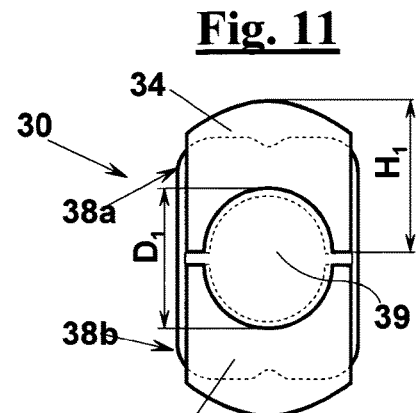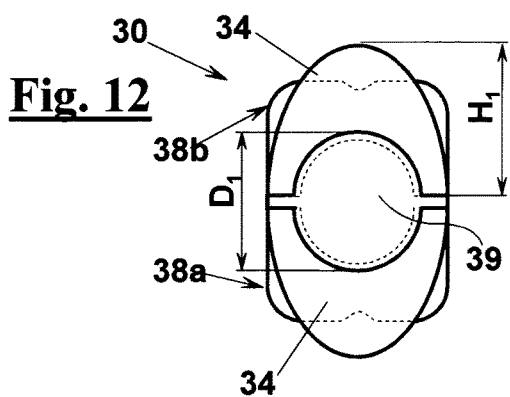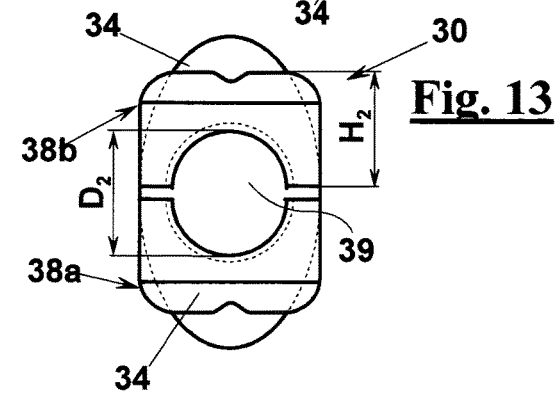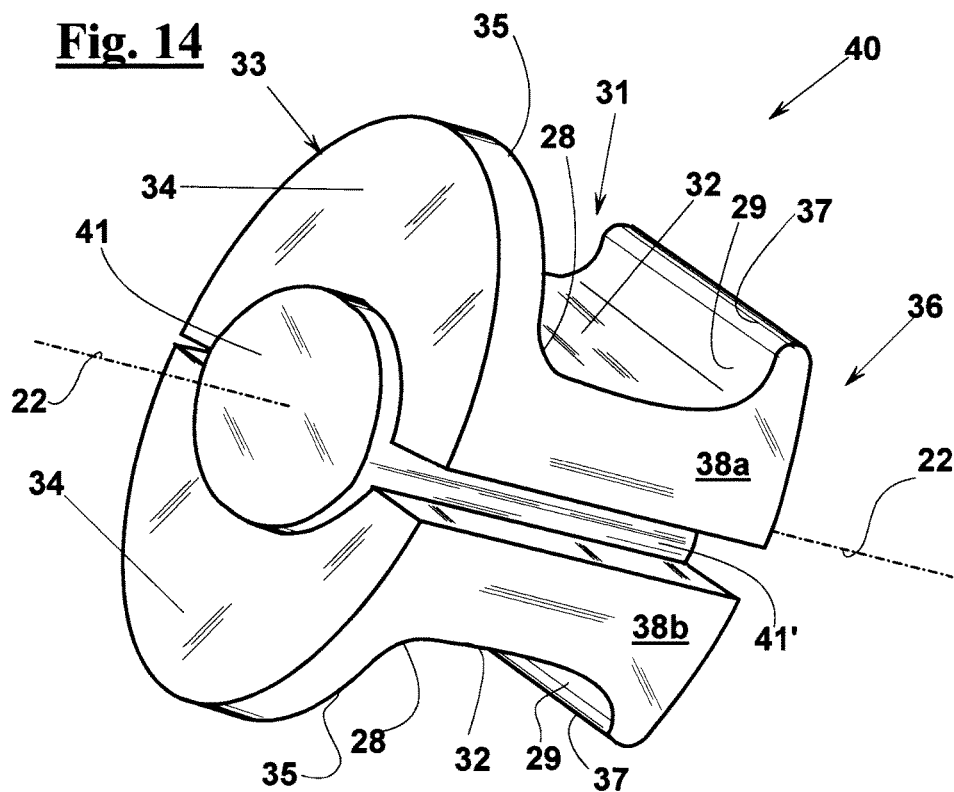

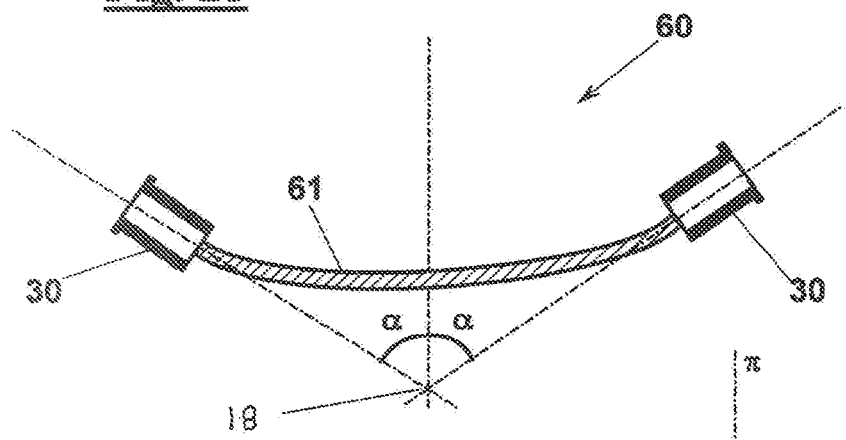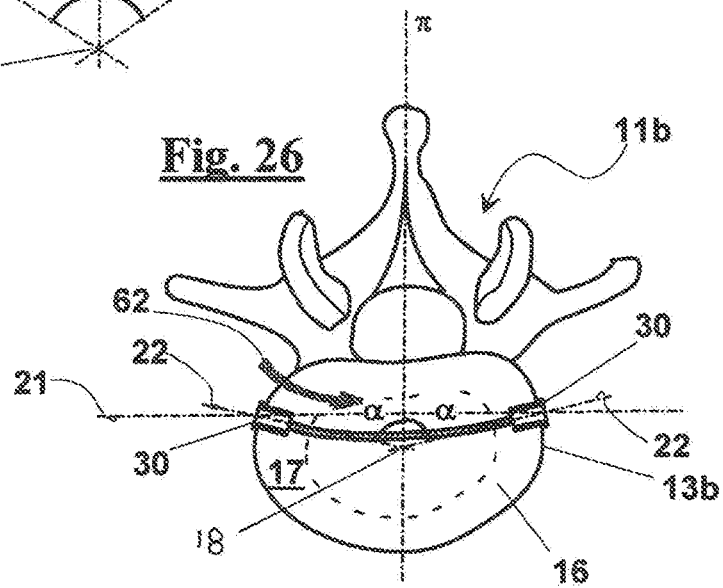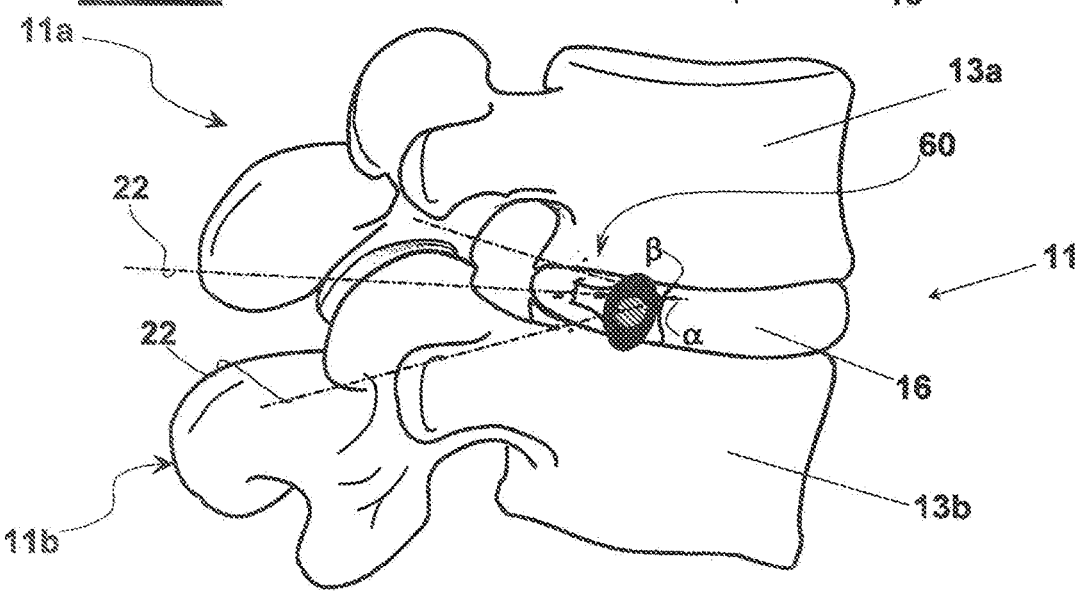

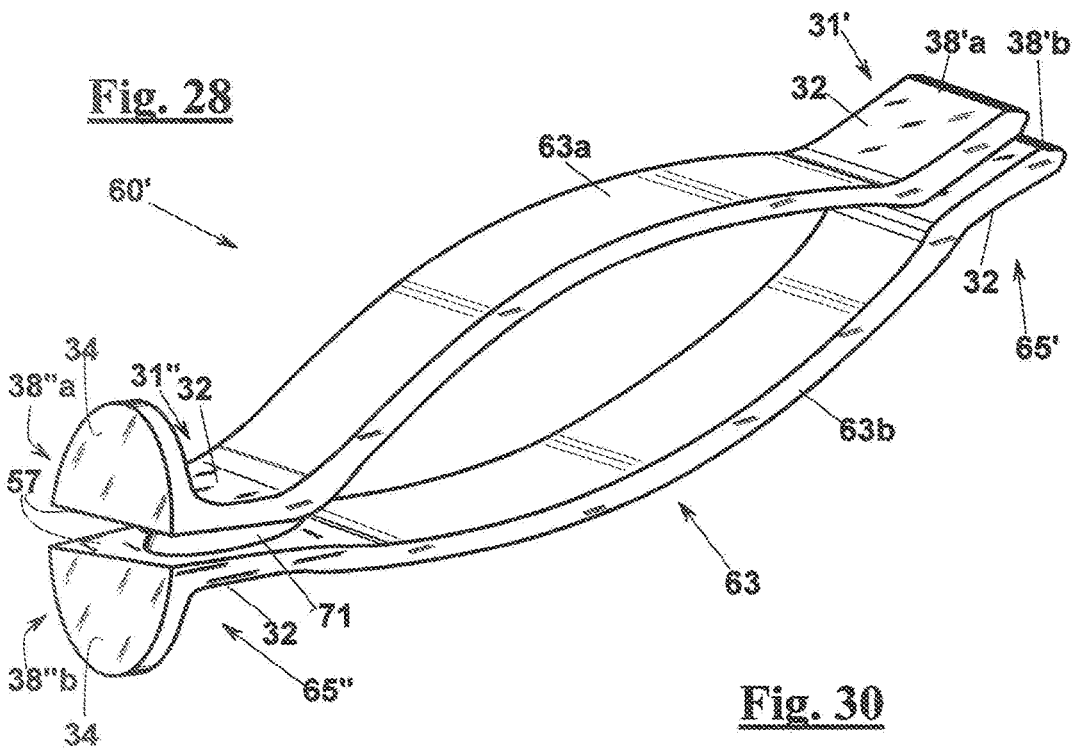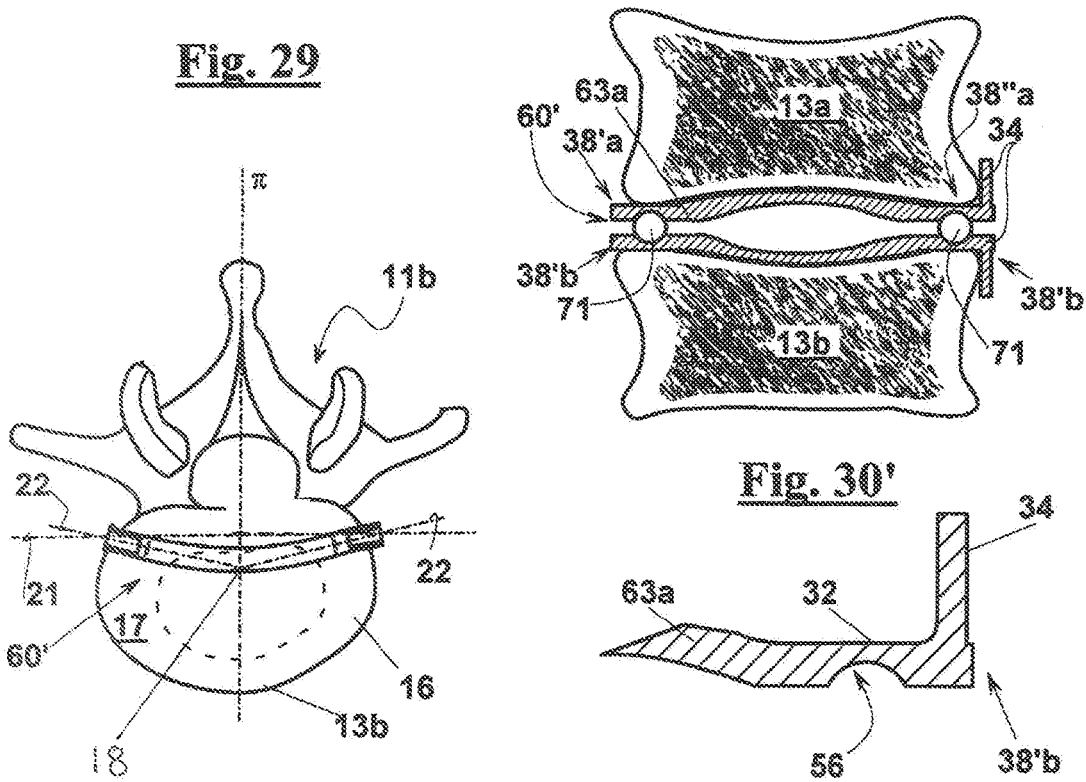

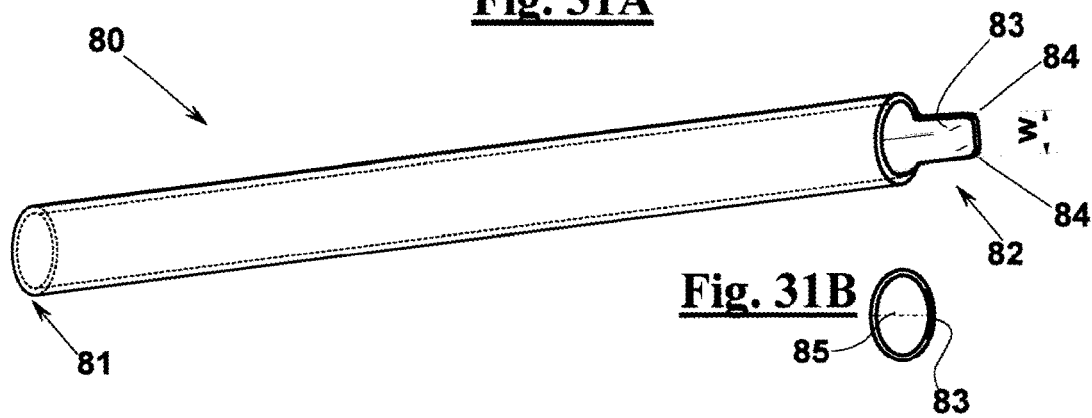
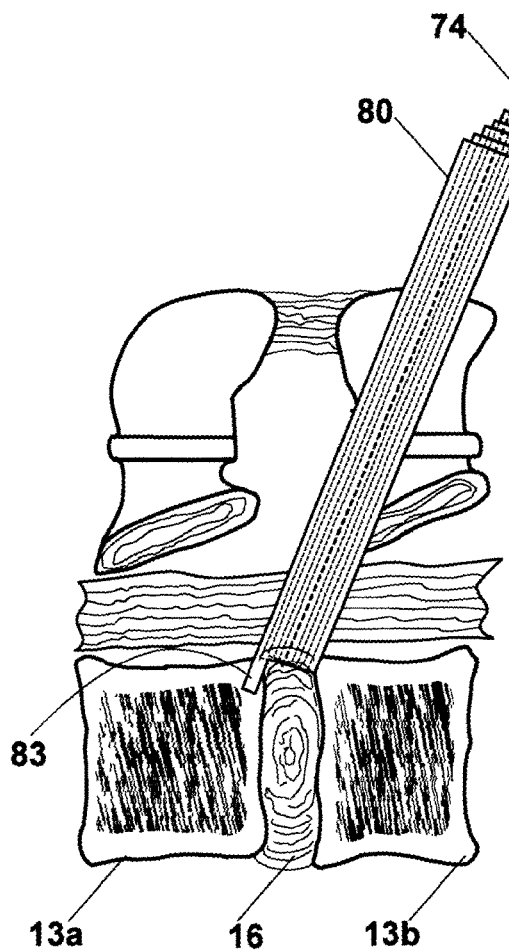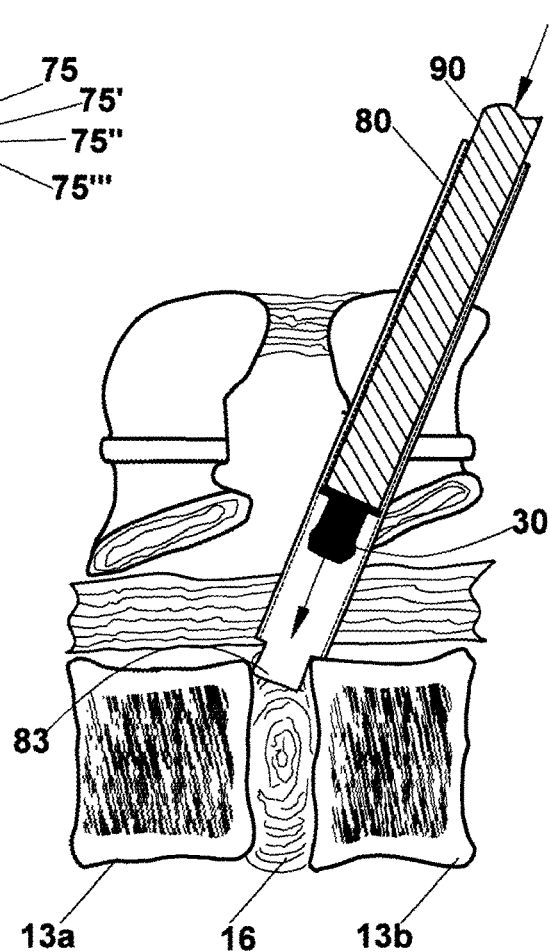

INTERVERTEBRAL SUPPORT

This application is a 371 of PCT/IB2011/001947, filed on Aug. 25, 2011, which claims priority to Italian Patent Application No. PI2010A000100, filed Aug. 26, 2010.

SCOPE OF THE INVENTION

The present invention relates, in general, to intervertebral supports and, more in particular, it refers to percutaneously implantable intervertebral supports.

BACKGROUND OF THE INVENTION

Intervertebral supports are known that provide a mutual support between vertebral discs that are overloaded and/or affected by various degenerative diseases. This reduces the loads acting on the discs. The use of intervertebral supports is a treatment alternative to the fusion of adjacent vertebrae, which consists of rigidly connecting to each other the vertebrae adjacent to a degenerated disc. This technique has the drawback of considerably reducing the mobility of the spine.

As shown in FIG. 1, an intervertebral support type is an interspinous support 10 is known that is configured to be arranged between the spinous apophysis 9a and 9b of two adjacent vertebrae 11a and 11b. Interspinous support 10 applies and receives forces to/from adjacent vertebrae 11a and 11b and reduces the load on the disc 16 that is located between them. For example, supports of this type are described in US2006/0271049 and in WO 2008/057838. Such supports provide a substantially immediate relief of pain to the patient, but are not suitable for stopping the degenerative breakdown of the disc and the vertebrae. In consequence, a segment of spine 11 that is affected by such a degenerative process is stabilized anomalously. Such condition is known as distability, and is caused by a shift of the instantaneous rotation axis 21 (FIG. 3). The relative movement of vertebrae 11a and 11b, i.e. the flexion-extension movement of spine 11, takes place about instantaneous rotation axis 21. In other words, the flexion-extension movement of the spine comprises a relative movement of adjacent vertebrae 11a and 11b that, over time, causes a local compression of intervertebral disc 16. This results into a damage of the pumping disc function, of the ligament system, and of the facet joints of vertebrae 11a and 11b.

As shown in FIG. 2, interlaminar supports 20 are also known, which are described, for example, in WO 2004/084743. The interlaminar supports are arranged between the laminae 8a and 8b of adjacent vertebrae 11a and 11b. By the interlaminar supports, the two adjacent vertebrae 11a and 11b are spaced apart from each other following a substantially translational movement, which limits the local overloads that act on disc 16. However, such devices can retard the degenerative breakdown, but are not well suited for ultimately block it. Moreover, the interlaminar space 14 is very close to the spinal channel 15, where the nervous tissue is present. For this reason the positioning of interlaminar supports can be a critical matter.

Furthermore, the surgical implant of the intervertebral supports requires a considerably large access, in order to provide a suitable visibility and to allow handling the instruments required for suitably distracting the vertebrae, and in order to maintain such distraction.

WO01/41681 describes an intervertebral support assembly comprising a pair of bone allografts that are positioned between two adjacent vertebrae, towards the front portion of these vertebrae, and also comprising a pair of facet screws, each screw securing together two facets of the two vertebrae. Such vertebral support system, as well as all fusion systems, has the drawback of stiffening the two adjacent vertebrae with respect to each other, which severely reduces the mobility of the spine.

U.S. Pat. No. 6,113,637 describes a prosthesis for an intervertebral disc comprising a ball portion and a concave portion that is configured to engage with a second vertebra close to the first vertebra. The concavity of the concave portion includes a substantially flat surface. When the two portions engage with the respective vertebrae, they engage with each other enabling a relative rotation and translation movement of the vertebrae. Both portions comprise a flange for engaging a respective vertebra. The prosthesis has the drawback treating insufficiently an affected disc at the beginning of the degenerative breakdown, when a functional recovery of the disc is still possible.

SUMMARY OF THE INVENTION

It is therefore a feature of the present invention to provide an intervertebral support that is adapted to resist and/or to stop the degenerative breakdown of an articular unit of the spine, and that is also adapted to relief the pain of a patient suffering from incipient or clear disc diseases.

It is also a feature of the present invention to provide such an intervertebral support that is adapted to follow the movement of the spine, such that a higher local mobility with respect to prior art devices is achieved.

It is also a feature of the present invention to provide such an intervertebral support that can be implanted percutaneously, and that requires a minimum access to this purpose.

These and other objects are achieved by an intervertebral support device configured to be arranged between two adjacent vertebral bodies of the spine of a patient, in such a way that a relative movement is allowed between said adjacent vertebral bodies and that said support device can contribute to bear the load of an upper vertebral body on a lower vertebral body, the vertebral bodies having a sagittal axis and a mid-sagittal plane, said adjacent vertebral bodies having a respective front half and a respective rear half, as these are defined by a coronal plane that passes through the median sagittal axis, and also having respective edge portions that face each other, the device comprising a couple of support elements, each support element of said support elements having a support surface, the support elements configured to be inserted between the edge portions of the respective rear half of the adjacent vertebral bodies such that the support surface engages with the edge portions, and assists to bear this load, and the support elements configured to be arranged at opposite sides of the edge portions with respect to the mid-sagittal plane, at respective angles centred on the sagittal axis and measured starting from the mid-sagittal plane, the angles set between 30° and 90°.

In particular, these angles are set between 45° and 75°.

In particular, the support element has a substantially prismatic or cylindrical shape.

Advantageously, the support elements are configured to be arranged at opposite sides of the edge portions with respect to the mid-sagittal plane, at respective angles such that each support surface is arranged at the instantaneous rotation axis of the natural relative flexion-extension movement of the two adjacent vertebrae.

The instantaneous rotation axis ideally crosses the edge portions of the vertebral bodies at points that are located at angles set within the above mentioned limits. Therefore, the device is adapted to support the two vertebral bodies at the relative instantaneous rotation axis between the two adjacent vertebrae. The instantaneous rotation axis is ideally the place where the distance between the vertebral bodies remains unchanged during the flexion-extension movement.

According to another point of view, the position of the two support elements is located proximate to the limit between the rear third portion and the medial third portion of the two adjacent vertebral bodies. This is normally also the position of the instantaneous rotation axis of the natural relative flexion-extension movement. The rear third portion is the third portion of the vertebral body part that is set between a line ideally connecting the pedicles to the vertebral body and the front apex of the vertebral body.

When positioning the support element at the instantaneous rotation axis of the natural relative flexion-extension movement, the relative flexion-extension and torsion movements of the two vertebrae are not significantly limited.

Furthermore, such an arrangement of the support elements prevents the instantaneous rotation axis from leaving its own natural position, which passes through for rear third portion of the vertebral bodies. The shift of the instantaneous rotation axis characterizes the first stage of the degenerative breakdown that a vertebral disc and the adjacent vertebrae can experience. If the instantaneous rotation axis is restored and/or stabilized at its natural location, the structures that control the loads acting on the articular unit are allowed to operate, and the degenerative breakdown is substantially blocked.

Various researches have shown that the restoration of the natural spine biomechanics can help to rehydrate the disc. The device according to the invention promotes such a restoration by correcting the position of the instantaneous rotation axis. Therefore, this device is useful for a functional recovery of an affected disc.

Therefore, the clinic indications to use the device according to the invention are the typical diseases of the first stage of the degenerative breakdown. In particular, these diseases are the following: discopathy at various stages, foraminal stenosis or soft stenosis, outcomes of discectomies in young patients.

Preferably, the support element has an overall length set between 8 and 18 mm, as measured between a first end of the support element and a second end opposite to the first end.

The definition of first end or first end portion of the support element refers to the end or the end portion which, in use, is located within an intervertebral space. The definition of second end or second end portion refers to the end or the end portion opposite to said first end or to said first end portion, so that said second end or said second end portion, in use, is arranged closer to the external surfaces of said edge portions of said vertebral bodies, in particular outside of the intervertebral space. In the following description, the first end or the first end portions are also called the medial end or the medial end portion, respectively. In the following description, the second end or the second end portions are also called as lateral or lateral end portion, respectively.

Preferably, the support element comprises a constraint means which constrains the support element to a vertebral body of the adjacent vertebral bodies, where the constraint means comprises a protruding part of the support element that protrudes with respect to the support surface, said protruding part configured to abut against an inner surface of the edge portion of the vertebral body and/or against an outer surface of the vertebral body. This way, the constraint means resists possible forces that tend to expel the support element from the intervertebral space or that, in any case, tend to displace it from the predetermined support position. In other words, the constraint means resists the reaction force that is exerted on the devices by the intervertebral disc, if this is present. The constraint means also resists the expulsion forces due to the movement of the spine.

In a particular exemplary embodiment, the protruding part configured to abut against an outer surface of the vertebral body comprises a flange or a couple of wings that extends in a substantially perpendicular way with respect to the support surface, at opposite sides with respect to the support surface.

At least said flange or at least one of these wings can comprise a through hole that is configured to receive a bone nail. Advantageously, each wing comprises at least one of such through holes. In particular, through holes are made through different wings and are symmetrically arranged with respect to the longitudinal middle plane of the device. The bone nails can be replaced by other well known fastening means to definitively or temporarily fasten the support element to the bone tissue.

The bone nails can be used as primary fixation means, i.e. they can fasten the support elements to the vertebral bodies in a first period of time after the implant, before secondary means are used to stabilize the implant through the support surfaces, as it will be made clearer below.

Preferably, the protruding parts or wings that are configured to abut against an outer surface of the vertebral body have each a maximum protrusion height set between 4 and 8 mm.

Preferably, a connection surface is provided between the support surface and the protruding part. This assists the anatomical support of the connecting portions in the space located between the external edges of the vertebral bodies and the boundary of the respective vertebral plates. The support of the support elements occurs therefore on a zone that has a remarkable compression strength, since the cortical bone is particularly thick and compact.

In a particular exemplary embodiment, the device according to the invention comprises a constraint means which constrains said support element to one of the vertebral bodies, where the constraint means is configured to create an adhesion of the support surface with the edge portion of the vertebral body.

In an exemplary embodiment, the constraint means comprises a friction engagement means between the support surface and the edge portion of the vertebral body. In particular, the support surface has a sawtooth profile.

In another exemplary embodiment of the constraint means, the surface of the support element, in particular the support surface exposes a material adapted to promote osseointegration, i.e. an osteoinductive material, in particular hydroxyapatite, silica or a material suitably functionalized to promote osseointegration. In other words, the longitudinal portions provide a scaffold that allows the growth of bone cells. This way, with the time, the surface of the support element is bound to the edge portions of the vertebral bodies.

According to another aspect of the invention, the support element comprises a transversal grip means configured to engage with the fibres of the annulus fibrosus of the intervertebral disc that is located between the two adjacent vertebral bodies. In particular, the transversal grip means can be percutaneously operated between a manoeuvre position, in which they are substantially contained within the support element, and an implant position, in which they protrude from the support element to firmly engage with the fibres.

Preferably, each support element comprises:
a first longitudinal portion and a second longitudinal portion, said first and second longitudinal portions preferably symmetric to each other, which both provide a support surface portion for edge portions of the upper and lower adjacent vertebral bodies, respectively, the support surface portion of the first longitudinal portion and the support surface portion of the second longitudinal portion having a predetermined relative position;
an interface means between the first longitudinal portion and the second longitudinal portion by which a mobility of the relative portion is left such that a plurality of relative positions are allowed according to a shape of the spine corresponding to a position and/or to a movement of the patient, in order to maintain a desired anatomic distance between the adjacent vertebral bodies. This way, the device according to the invention allows preserving a local mobility of the spine at the adjacent vertebrae between which the device is located, even if each longitudinal portion is integrally connected to a respective vertebral body.

In an exemplary embodiment, the interface means comprises a central bearing portion arranged between the first longitudinal portion and the second longitudinal portion, the central bearing portion made of a softer implantable material, i.e. of a material that has a lower elasticity modulus, the first and the second longitudinal portions made of a stiffer implantable material, i.e. of a material that has a higher elasticity modulus.

According to an exemplary embodiment, the central bearing portion has substantially the shape of a right cylinder. According to another exemplary embodiment, the central bearing portion has a substantially frusto-conical shape. The central bearing portion can also have a substantially prismatic shape.

Advantageously, the central bearing portion adheres to the first and to the second longitudinal portion of the device by a layer of an adhesive material. The adhesive material can be of a type compatible with the biological environment of the implant site, and can be a surgical adhesive of known type. Alternatively, the central bearing portion is caused to adhere to the first longitudinal portion and to the second longitudinal portion by a welding a part of the material of the central bearing portion and a part of the material of each longitudinal portion. This welding can be carried out according to a prior art process.

The softer implantable material of the central bearing portion can be a resilient material. In particular, the softer material can be a silicone. Preferably, the Shore hardness of this softer material is set between 60 and 80.

Alternatively, but not exclusively, the softer implantable material can be a shape-memory material. For example, the softer implantable material can be a Nickel-Titanium alloy. This assists the implant of the support element, since the support element can be compressed without being blocked at the edge portions of the vertebral bodies, when the implant is completed. Then, the support element recovers a height that is adapted to ensure a firm contact between the edge portions of the vertebral bodies.

In particular, the first and/or the second longitudinal portions are made of a material comprising Polyetheretherketone (PEEK).

The first and/or the second longitudinal portion can also be made of a material comprising an implantable carbon material.

Alternatively, but not exclusively, the first and/or the second longitudinal portions are made of titanium or of an alloy comprising titanium. Alternatively, but not exclusively, the first and/or the second longitudinal portions are made of tantalum or of a material comprising tantalum. The use of titanium and/or the tantalum is particularly well suited to avoid allergic reactions.

In another exemplary embodiment, the interface means between the first longitudinal portion and the second longitudinal portion comprises an element having a convex surface arranged between the first longitudinal portion and the second longitudinal portion, said protruding part configured to engage with respective inner concave surfaces of the first longitudinal portion and of the second longitudinal portion, and configured to allow a relative rotation of the first longitudinal portion and of the second longitudinal portion with respect to each other.

In particular, the element having a convex surface is selected from the group consisting of:
a cylindrical element configured to allow the relative rotation about a substantially longitudinal axis of the support element;
an ellipsoidal element, in particular a spherical element configured to allow a rotation which can be obtained as a combination of a rotation about a substantially longitudinal axis and of a rotation about a transverse axis of the support element.

The relative rotation thus allowed is particularly useful for preserving the torsional mobility of the adjacent vertebrae with respect to each other.

The interface means between the first longitudinal portion and the second longitudinal portion can also comprise a spring arranged between the first longitudinal portion and the second longitudinal portion, the spring resiliently deformable between a first position, where the distance has an implant value and a use position where the distance has a use value.

Advantageously, a mutual retaining means is provided for mutually retaining said cylindrical element and each of said longitudinal portions. For example, such means can comprise a slightly adhesive substance. This assists the implant of the support elements of the device into the intervertebral site.

In a further exemplary embodiment, the interface means between the first longitudinal portion and the second longitudinal portion comprises a convex surface, which is internal to the support element, of the first or of the second longitudinal portion, and a concave surface of the second and of the first longitudinal portion, respectively, the concave surface and the convex surface arranged to movably engage with each other, such that a relative rotation is allowed of the first longitudinal portion and of the second longitudinal portion with respect to each other.

In particular the convex and the concave surfaces are ellipsoidal surfaces, preferably the convex surface and the concave surface are spherical surfaces. This allows a relative rotation which can be obtained as a combination of a rotation about a longitudinal axis and of a rotation about a transversal axis of the intervertebral support device. Advantageously, the convex surface has a curvature radius that is shorter than the curvature radius of the concave surface, to assist the relative rotation.

Advantageously, the support element comprises a constraint means between the first longitudinal portion and the second longitudinal portion to maintain the support element in a spread-apart configuration, where first end portions of the first and of the second longitudinal portion, which face each other, are at a distance that is shorter with respect to a distance between second end portions, which face each other, of the first longitudinal portion and of the second longitudinal portion, the second end portions opposite to the first end portions of respective longitudinal portions. In particular, the constraint means comprises eyelets that are integral to respective medial ends of the first and of the second longitudinal portion of the support element, such eyelets configured to engage with a breakable element, such as a low-strength surgical wire or a longitudinal withdrawable element. During the implant procedure, the constraint means allow to maintain the support element in the spread-apart configuration. This assists the insertion of the support element between the edge portions of the vertebral bodies, as it is described more in detail hereinafter. Furthermore, the relative rotation that is allowed is particularly useful for preserving the relative torsion mobility of the adjacent vertebrae.

The interface means between the first longitudinal portion and the second longitudinal portion can be provided by a combination of means selected from the above mentioned means.

In an exemplary embodiment of the invention, the intervertebral support device comprises a mutual constraint means between the support elements of the couple of support elements, the constraint means arranged in use in a region located between adjacent vertebral bodies.

In an exemplary embodiment, only one of the support elements is provided with said couple of wings, so that said intervertebral support device can be inserted between the vertebral bodies without any substantial distraction of the vertebral bodies.

The constraint means can comprise a constraint element that consists of a first portion and of a second portion that are configured to abut against the vertebral plate of the upper vertebral body and against the vertebral plate of the lower vertebral body, respectively. In particular the first and the second portions comprise resilient parts or parts that are made of a shape-memory material.

In particular, the constraint element can be made of titanium or of an alloy comprising titanium, in particular a Nickel-Titanium alloy. Alternatively, but not exclusively, the first and/or the second longitudinal portions are made of tantalum or of a material comprising tantalum.

In another exemplary embodiment, the mutual constraint means between the support elements comprises a substantially stiff element that is integral to the support elements. In particular, the substantially stiff constraint element has a curved shape, where a face concave of the substantially stiff element is exposed laterally.

In an exemplary embodiment, the mutual constraint means between the support elements comprises a surgical wire, and the support elements comprise a fixation means for the surgical wire.

In an exemplary embodiment, the mutual constraint means can be disassembled from at least one of the support elements.

In a further exemplary embodiment, the mutual constraint means comprises a position adjustment means for adjusting the position of at least one support element of the couple of support elements with respect to the edge portions of the vertebral bodies and/or for adjusting the distance of a support element (30, 65', 65") with respect to the other support element of the couple of support elements. In particular, the position adjustment means comprises a screw threaded adjustment means.

The intervertebral support device, according to the various exemplary embodiments and according to the various aspects of the invention, can be implanted percutaneously. The implant requires one or two minimum size percutaneous accesses. Furthermore, the implant does not cause any damage to muscle and connective tissues of the back. This muscle tissues control the movement of the spinal column and the loads acting thereon, in particular in the lumbar zone.

A method is now described for implanting the vertebral support device according to the invention between two rear portions of the vertebral bodies of two adjacent vertebrae. In particular, the device according to the invention comprises two support elements, as described above. This method comprises the steps of:
  making two opposite side openings in the skin of the patient, at a level that corresponds to the intervertebral level between the two adjacent vertebral bodies;
  inserting a guide wire, typically a Kirschner wire, through this percutaneous opening, until the guide wire reaches the intervertebral space located between the two adjacent vertebral bodies;
  inserting a first surgical cannula on the guide wire through the opening, until the first surgical cannula reaches the intervertebral space access between the adjacent vertebral bodies, at the predetermined implant site;
  inserting surgical cannulas of increasing diameter in subsequent respective insertion steps, so that the surgical cannulas are concentrically arranged with respect to one another, until a last surgical cannula is inserted the diameter of which is long substantially as the distance between the edge portions of the adjacent vertebral bodies;
  inserting a working surgical cannula on the last surgical cannula, where said working cannula has a size larger than the diameter of the last surgical cannula and is adapted to slidingly receive within itself the support element according to the invention;
  extracting the guide wire and the surgical cannulas starting from the first cannula until the last cannula is extracted, and leaving the working surgical cannula in its position;
  inserting the support element into the working surgical cannula, until the support element reaches the access to the intervertebral space;
  inserting an elongated compression element or beater element into the working surgical cannula;
  pressing the beater element on the support element, until the support element is located at the predetermined surgical site between the adjacent vertebral bodies;
  extracting the beater element and the working surgical cannula.

The device can comprise two support elements to be located at implant positions opposite to each other with respect to the mid-sagittal plane of the patient. In this case, the previous steps are advantageously carried out at the same time for the two support elements, through respective percutaneous side openings and accesses towards to the respective implant sites.

The scope of the invention also includes a working surgical cannula for a support element as described above, which has a manoeuvre end portion and a positioning end portion for positioning at a surgical implant site located between the edge portions of two adjacent vertebral bodies, where the positioning end portion has a side tang extension that is configured to be inserted between the edge portions of the adjacent vertebral bodies. The side tang extension has a width, with respect to the insertion direction, that is adapted to cause a predetermined distraction between the adjacent vertebral bodies at the surgical site, by pressing the working surgical cannula against said two adjacent vertebral bodies. This assists the insertion of the support element into the surgical implant site.

Preferably, the tang portion of the working surgical cannula has rounded end edges. Advantageously, the working surgical cannula is made of a plastic material. this assists the introduction between the vertebral bodies and distraction of the latter, and prevents the edge portions of the adjacent vertebrae from adhesions.

In particular, the working surgical cannula has a substantially elliptical cross section, such that the working surgical cannula can receive a support element that has a substantially elliptical outer profile, and the insertion tang portion occupies a position proximate to the minor axis of the substantially elliptical cross section.

Preferably, the working surgical cannula that is used in the method for implanting the above described vertebral support device is the previously described surgical cannula.

Advantageously, a step is provided of rotating the surgical cannula for arranging the introduction tang portion along a direction that is transversal with respect to the intervertebral space access.

Advantageously, at least one of the above described steps is carried out under scopic control, with radiographic assistance.

This way, the support element or the support elements of the intervertebral device according to the invention are implanted percutaneously, i.e. in a minimally invasive approach.

In particular, the support element can have a spread-apart configuration in which the distance between the medial ends is shorter than the distance between the lateral ends of the first longitudinal portion and of the second longitudinal portion. Before the step of introducing the support element into the working surgical cannula, a step is therefore provided of:

prearranging the constraint means between the first longitudinal portion and the second longitudinal portion, such that the support element is maintained in the spread-apart configuration until the support element achieves the intervertebral space access, and a step of:

removing the constraint means, so that the support element can leave the spread-apart configuration once it has been inserted into the surgical implant site between the vertebral bodies. The step of removing the constraint means can comprise breaking a breakable element that maintains the medial ends of the two elements longitudinal joined to each other. For instance, the breakable element can be a thin surgical wire. Otherwise, the step of removing the constraint means can comprise extracting a longitudinal element from a mutual engagement seat at the medial ends of the two longitudinal elements. This way, the implant can be performed with a minimum preliminary distraction of the vertebral bodies.

The scope of the invention also includes a beater element, which is configured to be inserted into the working surgical cannula, which is provided with a clamping means that is configured to engage with a seat at the lateral end of the support element, in order to maintain the support element in the spread-apart configuration. By releasing the clamping means, the reaction of the support element to the compression applied by the beater element causes the support element to close within its own surgical implant site. Then, the support surfaces and the medial ends penetrate between the edge portions of the vertebral bodies.

Advantageously, in the case of a support element that can have a spread-apart configuration, the step of inserting a beater element into the working surgical cannula provides the use of a beater element of the type specified above. The step of removing the constraint means is followed by a step of:

releasing the clamping means, such that the reaction of the support element to the compression causes the support element to close in its own surgical implant site. Then, the support surfaces and the medial ends penetrate between the edge portions of the vertebral bodies.

BRIEF DESCRIPTION OF THE DRAWINGS

The invention will be made clearer with the description of exemplary embodiments thereof, exemplifying but not limitative, with reference to the attached drawings, in which:

FIG. 10 is an elevational side view with dimensions of the support element of FIG. 4;

FIGS. 11 and 12 are front views with dimensions of two support elements according to two examples of an exemplary embodiment of FIG. 4, which have a different outline of the wings of the proximal portion;

FIG. 13 is a rear view with dimensions of a support element according to a variant of an exemplary embodiment of FIG. 4;

FIG. 14 is a perspective view of a support element of a device according to another exemplary embodiment of the invention;

FIG. 16 is a perspective view of a portion of a spine with a support element according to the exemplary embodiment of FIG. 14 or of FIG. 15;

FIG. 25 shows a device according to an exemplary embodiment of the invention, where two support elements are joined together by a constraint element;

FIG. 26 is a cross sectional view of an implant comprising a couple of support elements according to the exemplary embodiment of FIG. 25, showing an access path for the implant;

FIG. 27 is a perspective view of two adjacent vertebrae with a support element according to the exemplary embodiment of FIGS. 25 and 26;

FIG. 28 shows a device according to another exemplary embodiment of the invention, where two support elements are joined together by a constraint element;

FIGS. 29 and 30 are cross sectional views of an implant of a support element according to FIG. 28;

FIG. 30' is a cross sectional view of a detail of the support element of FIG. 30;

FIG. 31A is a perspective view of a working surgical cannula for a support element according to the invention;

FIG. 32B is an elevational front view of the working surgical cannula of FIG. 28A;

FIGS. 32A and 32B diagrammatically show the steps of a method for implanting a device according to an exemplary embodiment of the invention;

DESCRIPTION OF A PREFERRED EXEMPLARY EMBODIMENT

Figure 4:
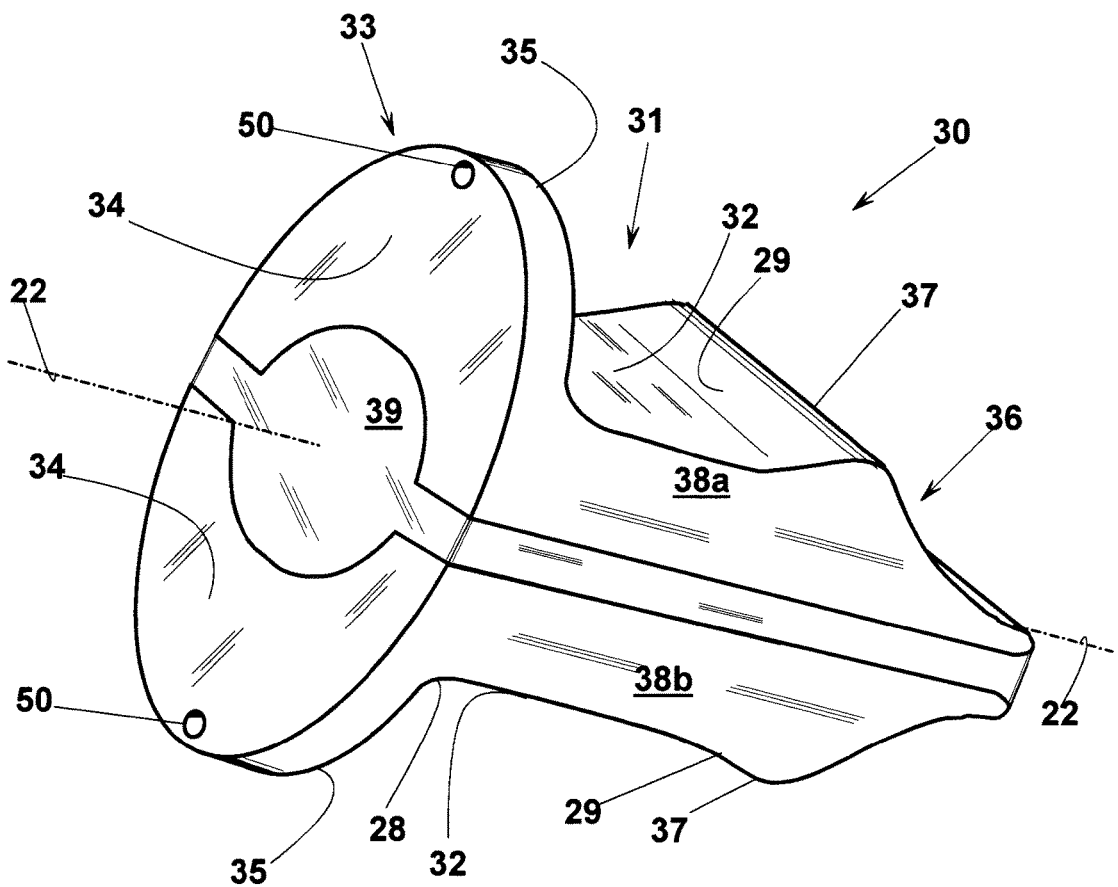
FIG. 4 is a perspective view of a support element of a device according to an exemplary embodiment of the invention.
Figure 5:
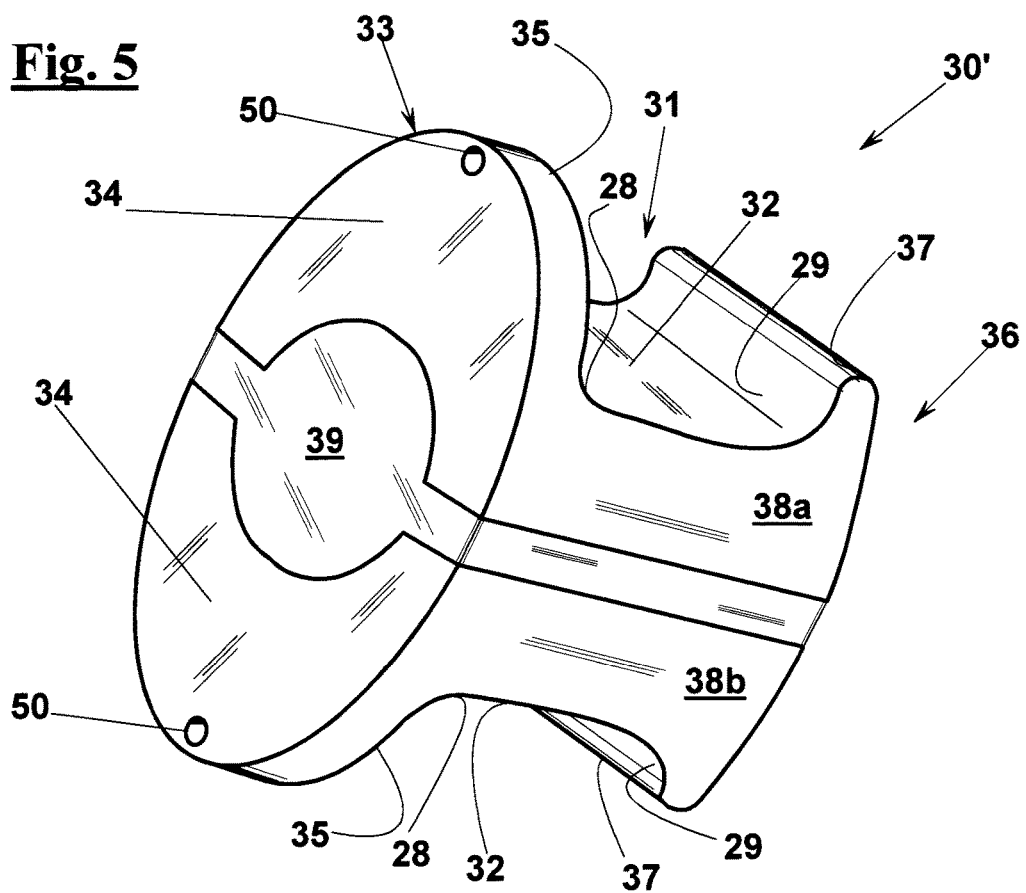
FIG. 5 shows a perspective view of an exemplary embodiment of the support element of FIG. 4.

With reference to FIGS. 4 and 5, a support element 30, 30' of an intervertebral support device is described according to two examples of a first exemplary embodiment of the invention. Support element 30, 30' has an elongated shape and extends along an axis 22. Support element 30, 30' is configured to be inserted between edge portions 53a, 53b of rear halves 13"a, 13"b of adjacent vertebral bodies 13a, 13b of a patient's spine 11, as diagrammatically shown in FIGS. 6 and 7.

Support element 30, 30' has a central elongated portion 31 that provides support surfaces 32 for adjacent vertebral bodies 13a, 13b.

Figure 7:
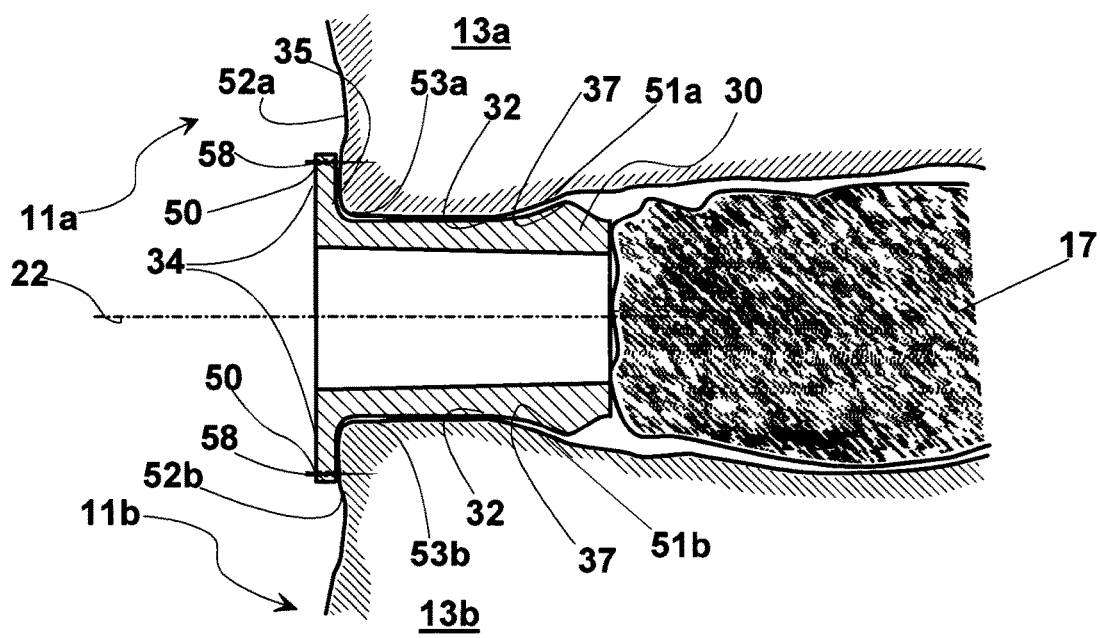
FIG. 7 is a cross sectional view of an implant of a support element according to FIG. 4.

In the shown example, support element 30, 30' comprises a medial end portion 36. Medial end portion 36 comprises protruding parts 37 which protrude with respect to support surface 32. In use, protruding parts 37 abut against respective inner surfaces 51a, 51b of adjacent vertebral bodies 13a, 13b. As FIG. 7 shows more in detail, protruding parts 37 oppose the expulsion of support element 30, 30', which can occur due to the movement of two adjacent vertebral bodies 13a, 13b against which support element 30, 30' abuts. Connection surfaces 29 are preferably provided between protruding parts 37 and support surfaces 32 (FIGS. 4 and 5) to assist the anatomical support of vertebral bodies 13a, 13b.

Still in the examples shown in FIGS. 4 and 5, support element 30, 30' comprises a substantially flat lateral end portion 33, for example a flange portion comprising two protruding parts 34 that protrude with respect to support surface 32. Protruding parts 34 can have the shape of two wings that extend at opposite sides of support element 30, 30', substantially along planes that are perpendicular to respective support surfaces 32. As FIG. 7 shows, wings 34 have rear faces 35 in use abutting against external surfaces 52a, 52b of adjacent vertebral bodies 13a, 13b. This way, support element 30, 30' is firmly positioned between edge portions 53a, 53b.

Connection surfaces 28 (FIGS. 4 and 5) are preferably provided between protruding parts 34 and support surfaces 32, to assist the anatomical support of vertebral bodies 13a, 13b on faces 52a, 52b. In particular, the shape of connection surfaces 28 is congruent with the connection between external surfaces 52a, 52b of vertebral bodies 13a, 13b and edge portions 53a, 53b of the respective vertebral bodies.

In an exemplary embodiment, as shown in FIG. 4 and in FIG. 5, one or both protruding parts 34 of support element 30, 30' comprise/s respective holes 50. Holes 50 are preferably made at positions that are symmetrical with respect to the middle plane of support element 30, 30'. Holes 50 serve for housing respective fixation means that are adapted to anchor at external surfaces 52a, 52b of respective vertebral bodies 13a, 13b. The fixation means can be small bone needles, i.e. conventional spikes.

Lateral end portion 33 and medial end portion 36 can cooperatively provide a constraint means which constrains support element 30, 30' to vertebral bodies 13a, 13b. The constraint means is adapted to oppose the reaction forces that are applied by the intervertebral disc 16 (FIGS. 3 and 7) on vertebral support elements 30, 30', and also the expulsion forces that are created by the physiological movement of spine 11.

Still with reference to the exemplary embodiment of FIGS. 4 and 5, vertebral support element 30, 30' is obtained by connecting two longitudinal support halves 38a, 38b with a central bearing member 39 arranged between the two longitudinal support halves. In the example shown, longitudinal support halves 38a, 38b are equal to each other and are arranged symmetrically with respect to each other. Central bearing member 39 forms an interface means between the support halves 38a, 38b that allows a mobility of the relative position of the support halves 38a, 38b and therefore a mobility of respective support surfaces 32. This way, support surfaces 32 can have in use a plurality of relative positions. These relative positions depend on the movement of the spine functionality of the subject who bears the support. This way, an anatomic distance is maintained between adjacent vertebrae 11a, 11b (FIGS. 6 and 7), in any possible position of spine 11.

In an exemplary embodiment of support elements 30, 30', the support halves 38a, 38b are made of a substantially stiff implantable material. An implantable material is a material that has a biological compatibility suitable for building an implant. In particular, the implantable material can comprise Polyetheretherketone (PEEK), or implantable carbon material.

Alternatively, but not exclusively, support halves 38a, 38b are made of titanium, or of tantalum. Titanium and tantalum have a high biologic compatibility. Support halves 38a, 38b can be made of a titanium alloy and/or of tantalum as well.

Figure 8:
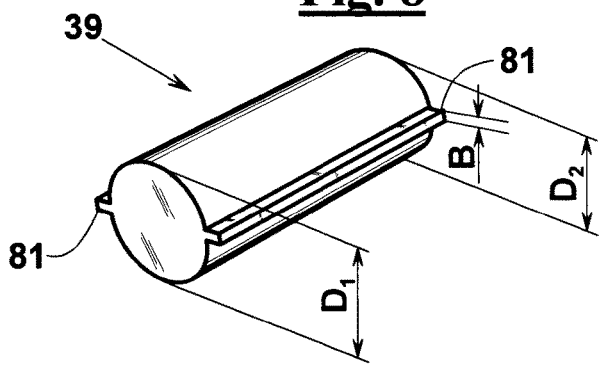
FIG. 8 is a perspective view of a central bearing portion of the support element of FIG. 4 or of FIG. 5.

With reference to FIG. 8, an exemplary embodiment is shown of central bearing portion 39. In this example, central bearing portion 39 has a substantially frusto-conical shape, with respective major and minor diameters $D_1$ and $D_2$. In another exemplary embodiment that can be seen in FIG. 8, central bearing portion 39 has a substantially cylindrical shape, and the two diameters $D_1$ and $D_2$ coincide in a same value. In an exemplary embodiment, not shown, central bearing portion 39 has a prismatic shape. Portion 39 has two symmetrical diametrical protruding parts 81 of height B. Symmetrical diametrical parts 81 are suitable for introduction between substantially flat portions 55 of the inner faces of support halves 38a (or 38b, FIGS. 23 and 24). This way, a transverse continuity is obtained of bearing 39, which is arranged between two support halves 38a, 38b.

In an exemplary embodiment of support elements 30, 30', bearing 39 is made of an implantable material that is softer than the material of support halves 38a, 38b. In particular, bearing 39 is made of silicone rubber, preferably in a silicone rubber of Shore hardness set between 60 and 80. Even more preferably, bearing 39 is made of a silicone rubber of Shore hardness of about 70. In alternative, but not exclusively, bearing 39 is made of an implantable material shape-memory, such as a Nickel-Titanium alloy.

Figure 9:
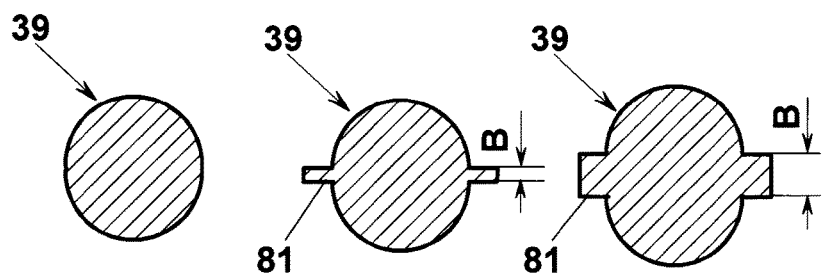
FIG. 9 shows a cross section of exemplary embodiments of the central bearing portion of FIG. 8.

In FIG. 9 a cross sectional view is shown of exemplary embodiments of bearing portion 39. In a first example, no protruding parts are provided which protrude with respect to the body of the bearing portion. In other examples, the protruding parts can have a height suitably lower than the overall height of bearing portion 39.

With reference to FIGS. 10 to 13, preferable sizes are shown of two longitudinal support halves 38a, 38b of support element 30 of FIG. 4. A length L (FIG. 10) of support element 30 is preferably set between 8 and 18 mm, measured between the external surfaces of the medial end portion and the external surfaces of the lateral end portion. In particular, the length L is set between 10 and 15 mm, more in particular length L is about 12 mm. A height H, measured between support surfaces 32, is preferably set between 4 and 12 mm, in particular height H is set between 8 and 10 mm. Furthermore, a height $H_1$ of wings 34 of each side portion 33 (FIGS. 11 and 12) is preferably set between 4 and 8 mm. The above figures also show a height $H_2$ of protruding parts 37 of medial portion 36, and diameters $D_1$ and $D_2$ of central bearing portion 39.

Figure 19:
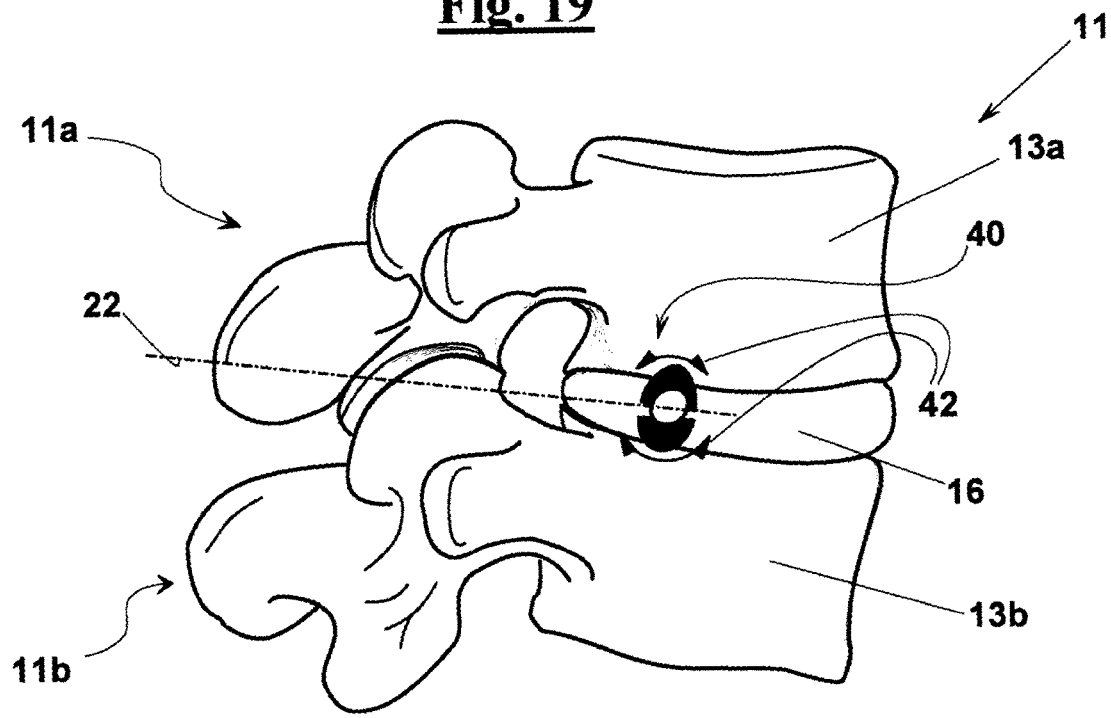
FIG. 19 is a perspective view of two adjacent vertebrae with a support element according to the exemplary embodiment of FIG. 14.

With reference to FIG. 14, a support element 40 is described according to another exemplary embodiment of the invention. Support element 40 comprises three portions that, in use, are mounted on one another. Such portions comprise two opposite longitudinal support halves 38a, 38b, in particular support halves 38a, 38b are identical and, in use, are arranged symmetrically. Support element 40 also comprises a cylindrical element 41 that has a cylindrical interface surface 41', which is configured to allow a relative rotation of two support halves 38a, 38b about longitudinal axis 22 of support element 40. This rotation is carried out as indicated by arrows 42 of FIG. 19. Due to this relative rotation, cylindrical element 41 allows changing the relative position of support halves 38a, 38b, such that the relative inclination of two support surfaces 32 can be adjusted. Therefore, support surfaces 32 can have a plurality of use relative positions. The use relative position depends on the shape of spine 11, which in turn depends on the movement and on the position of the patient. This way, an anatomic distance is always maintained between adjacent vertebrae 11a, 11b, as shown in FIG. 19.

Even if support halves 38a, 38b of device 40 of FIG. 14 are equal to support halves of device 30' of FIG. 5, they can have a different shape. For instance, they can be similar to support halves 38a, 38b of device 30 (FIG. 4). In particular, support halves 38a, 38b can be have the sizes shown in FIGS. 10 to 13.

Figure 15:
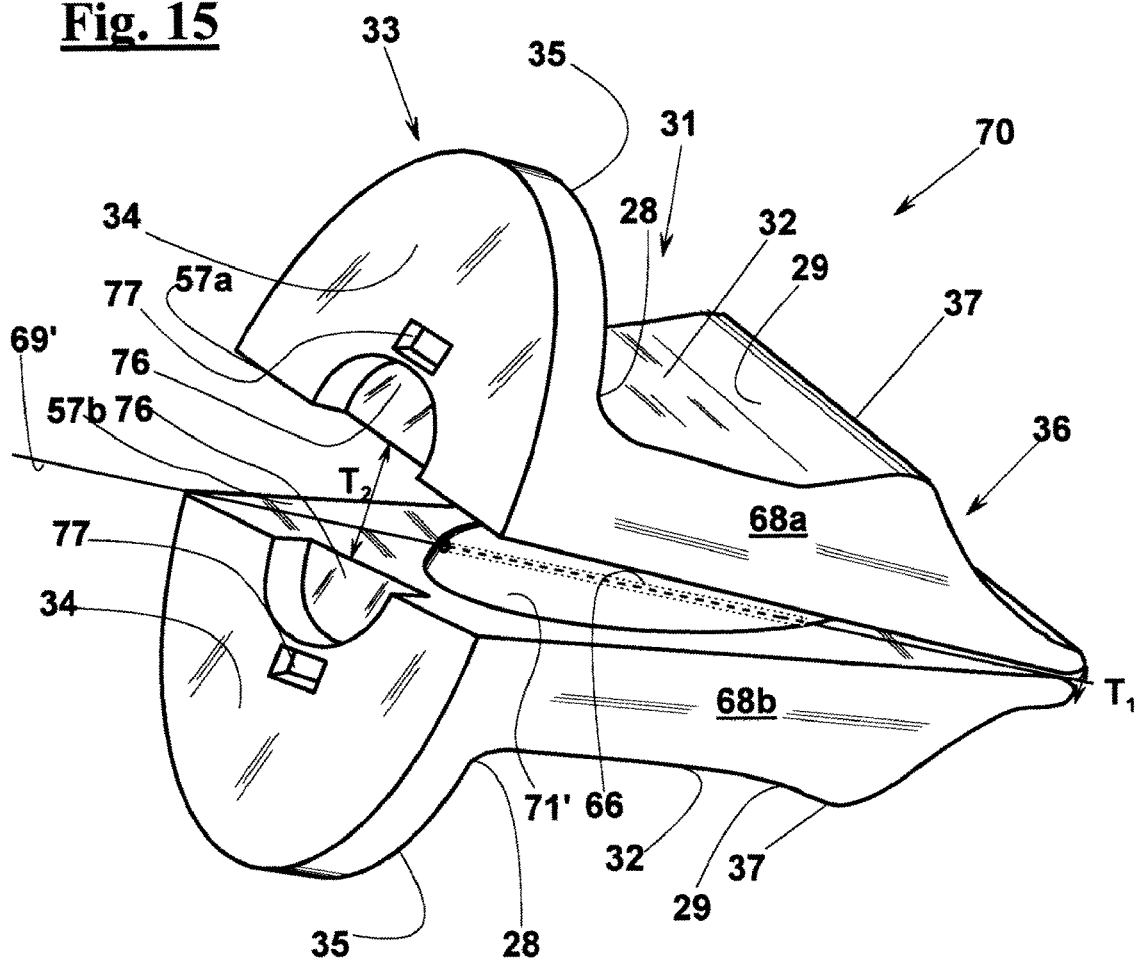
FIG. 15 is a perspective view of a support element of a device according to another exemplary embodiment of the invention.
Figure 16:
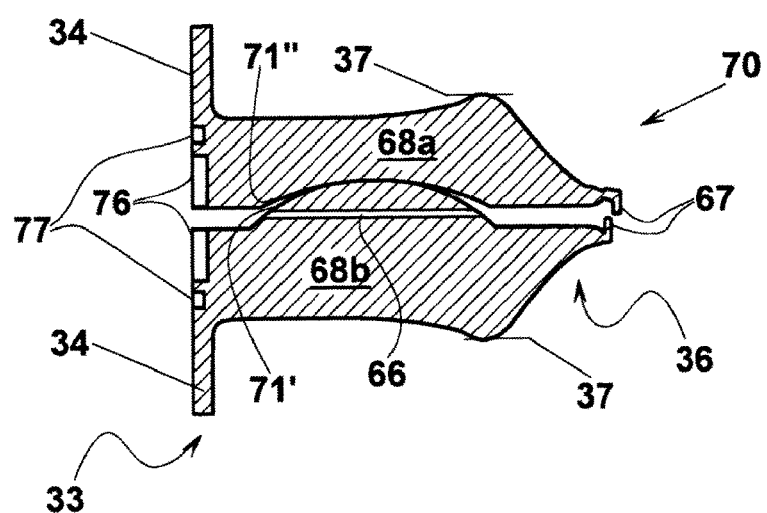
FIG. 16 is a longitudinal cross sectional view of the support element of FIG. 15.

With reference to FIGS. 15 and 16, a device 70 is described according to another exemplary embodiment of the invention. Device 70 is made of two different portions that are joined together for use. Such portions comprise two support halves 68a, 68b. The external surfaces of support halves 68a, 68b, comprising support surfaces 32, are similar to the external surfaces of support halves 38a, 38b of device 30. However the external surfaces can also have a different outline, for example the external surfaces can have an outline similar to the external surfaces of support halves 38a, 38b of support element 40 (FIG. 14). Two support halves 68a and 68b can have respective inner articulation surfaces 71', 71" (see also FIG. 16). Inner articulation surfaces 71', 71" can allow a relative movement between two support halves 68a and 68b, which can comprise rotations according to different axis. Such rotations take place as indicated by arrows 72 and 73 of FIG. 20.

Figure 20:
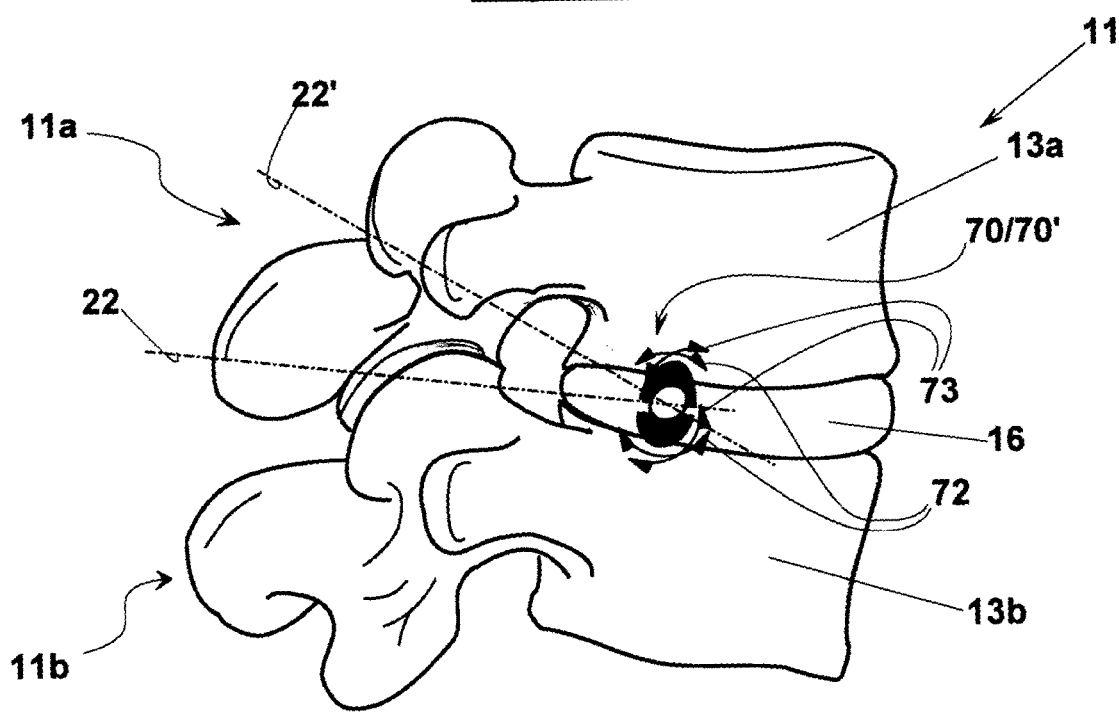
FIG. 20 is a perspective view of two adjacent vertebrae with a support element according to the exemplary embodiments of FIG. 15 or of FIG. 17.

In the exemplary embodiment of FIGS. 15 and 16, the articulation elements comprise a convex articulation surface 71' of an inner face 57b of support element 68b and a concave articulation surface 71" of an inner face 57a of support element 68a. In particular, concave articulation surface 71" has curvature radius longer than convex articulation surface 70. This way, a point contact is ideally obtained between articulation surfaces 71' and 71". Articulation surfaces 71' and 71" allow changing the relative position of support halves 68a, 68b, such that the relative inclination of two support surfaces 32 can be adjusted. Therefore, support surfaces 32 can have a plurality of use relative positions. The use relative position depends on the movement of the spine functional unit of the patient. This way, an anatomic distance is always maintained between adjacent vertebrae 11a, 11b, as shown in FIG. 20.

Figure 33:
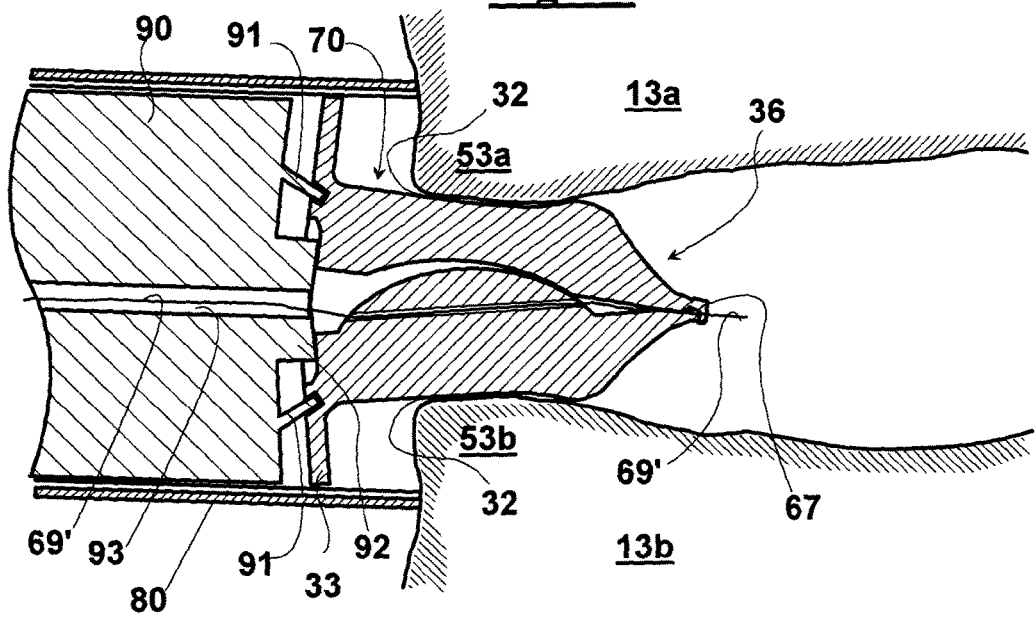
FIGS. 33 and 34 diagrammatically show the steps of a method for implanting a device according to another exemplary embodiment of the invention.
Figure 34:
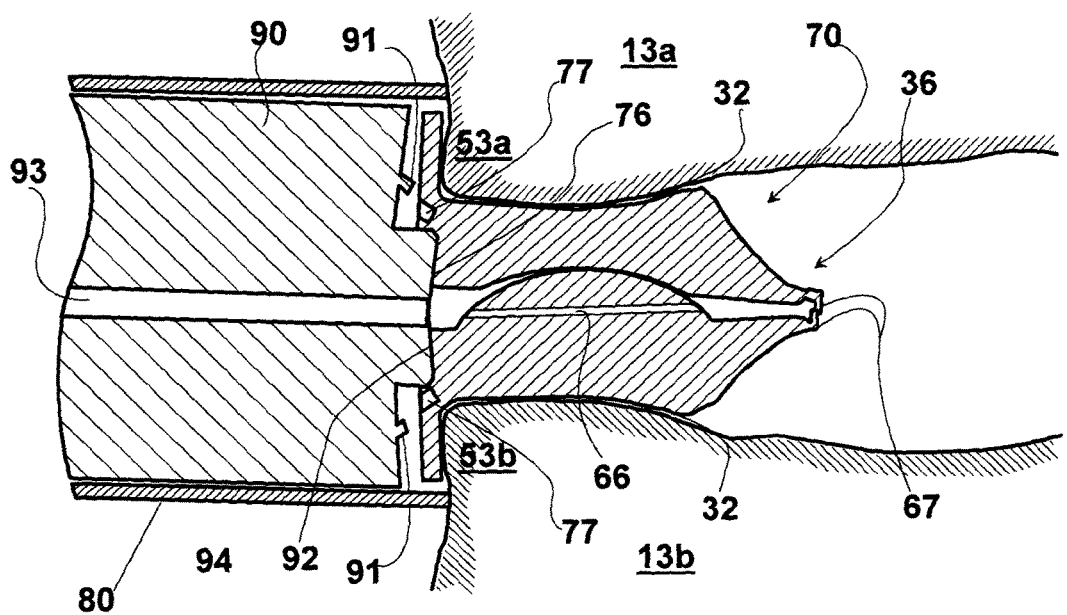

Even if support halves 68a, 68b of device 70, 70' of FIGS. 15 and 16 are equal to support halves of device 30 (FIG. 4), they can have a different shape. For instance, they can be similar to support halves 38a, 38b of device 30' of FIG. 5. Two housings 76 are provided on the outer face of lateral end portion 33 that are configured to receive a compression tool or a beater, as shown in FIGS. 33 and 34. In this exemplary embodiment, the two housings have an overall cylindrical shape and suitably protrude into respective support halves 68a, 68b, along the longitudinal direction of such halves. Two housings 77 are also provided on the outer face of end 33, on opposite halves that are configured to receive the gripping ends of a gripper. The gripper is used to maintain the support element 70 fastened about the beater of FIGS. 33 and 34.

Figure 17:
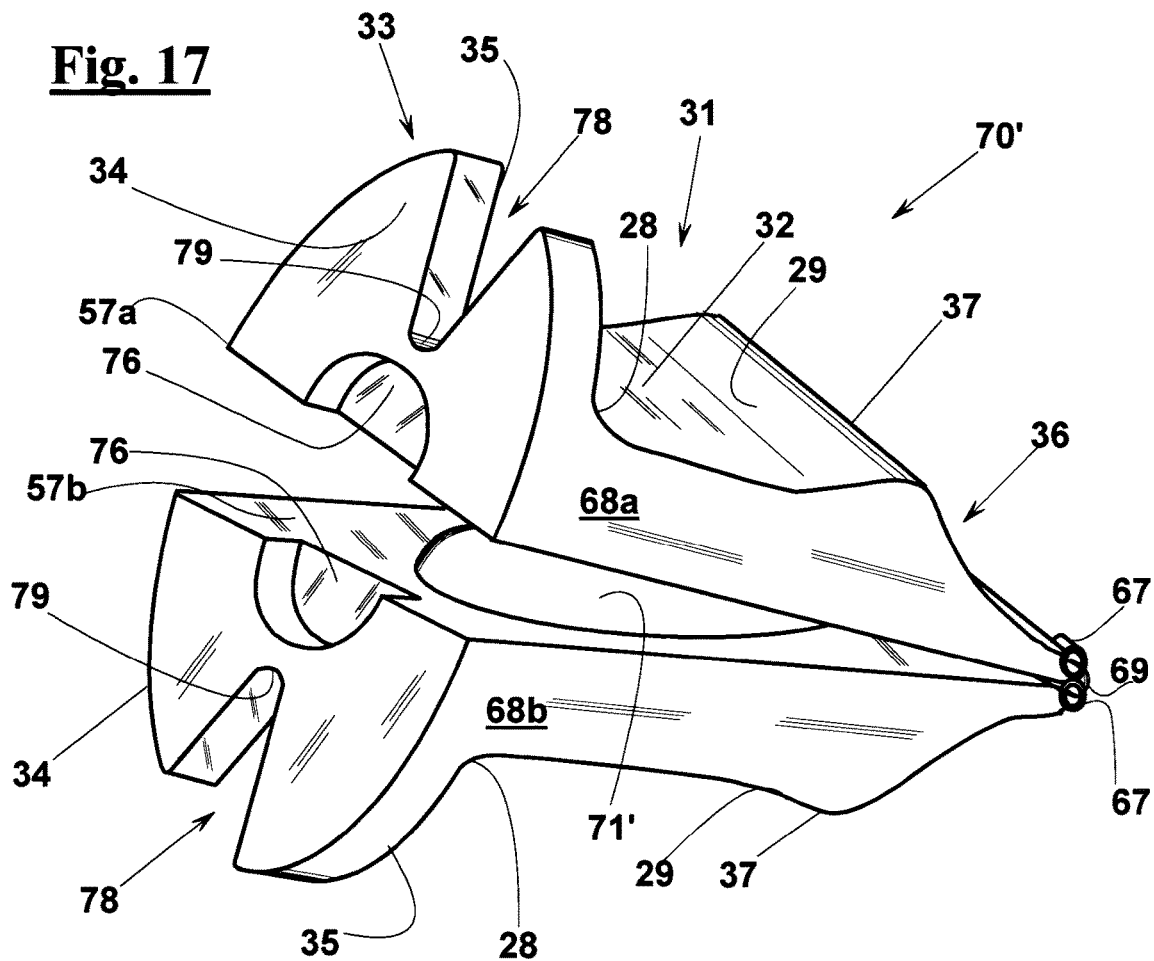
FIG. 17 shows a perspective view of a support element according to a further exemplary embodiment of FIG. 15.
Figure 18:
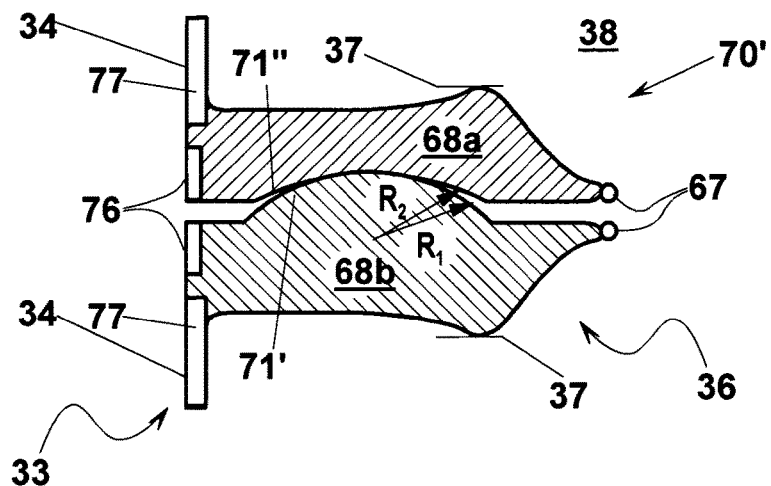
FIG. 18 is a longitudinal cross sectional view of the support element of FIG. 17.

With reference to FIGS. 17 and 18, an exemplary embodiment 70' of the device is described according to the exemplary embodiment of FIGS. 15 and 16. Device 70' differs from device 70 for the presence of V-passages 78 for gripping the ends of the gripper. The gripping ends engage housings that extend along grooves 79 of such V-passages up to rear faces 35 of wings 34.

Still with reference to FIGS. 15-18, an exemplary embodiment that is now described differs from exemplary embodiments 70 and 70' in that articulation surfaces 71' and 71" are replaced by a convex element 71 (see also FIG. 30), i.e. by an element that has convex surfaces. Convex element 71 can be substantially spherical, or can have the shape of an ellipsoid, and is housed between two concave surfaces 56 (FIG. 30') of inner faces 57a, 57b of support halves 68a, 68b. The support halves can be equal to half 68a. In such a half, at least one of concave surfaces 56 has preferably a curvature radius that is longer than the curvature radius of the substantially spherical or ellipsoidal element.

Figure 1:
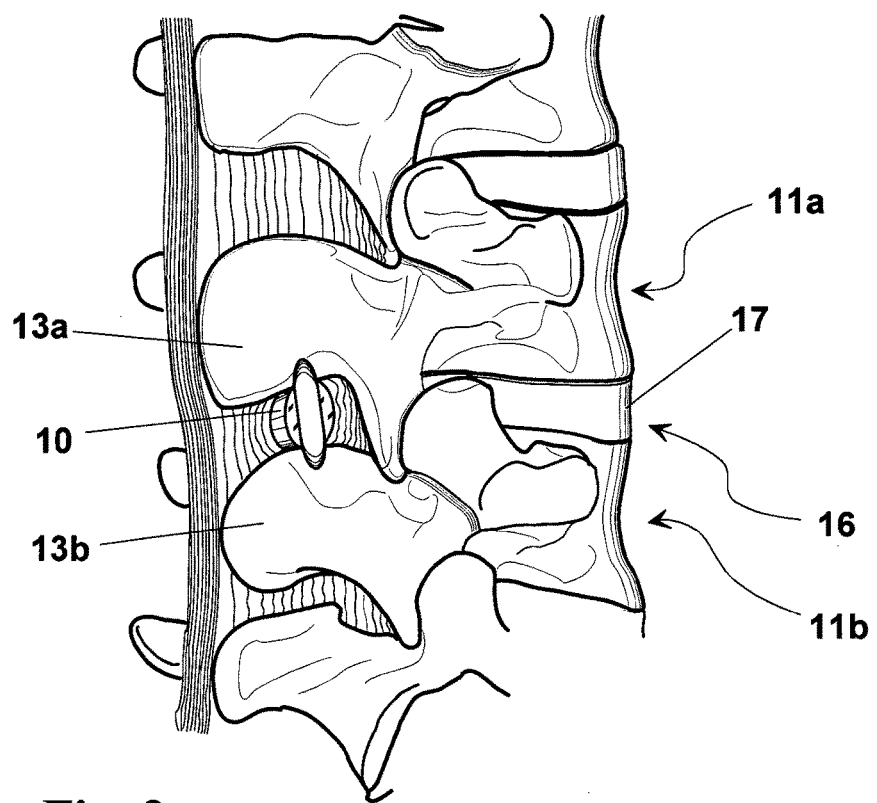
FIG. 1 is a perspective diagrammatical view of an implant of a prior art interspinous intervertebral support.
Figure 2:
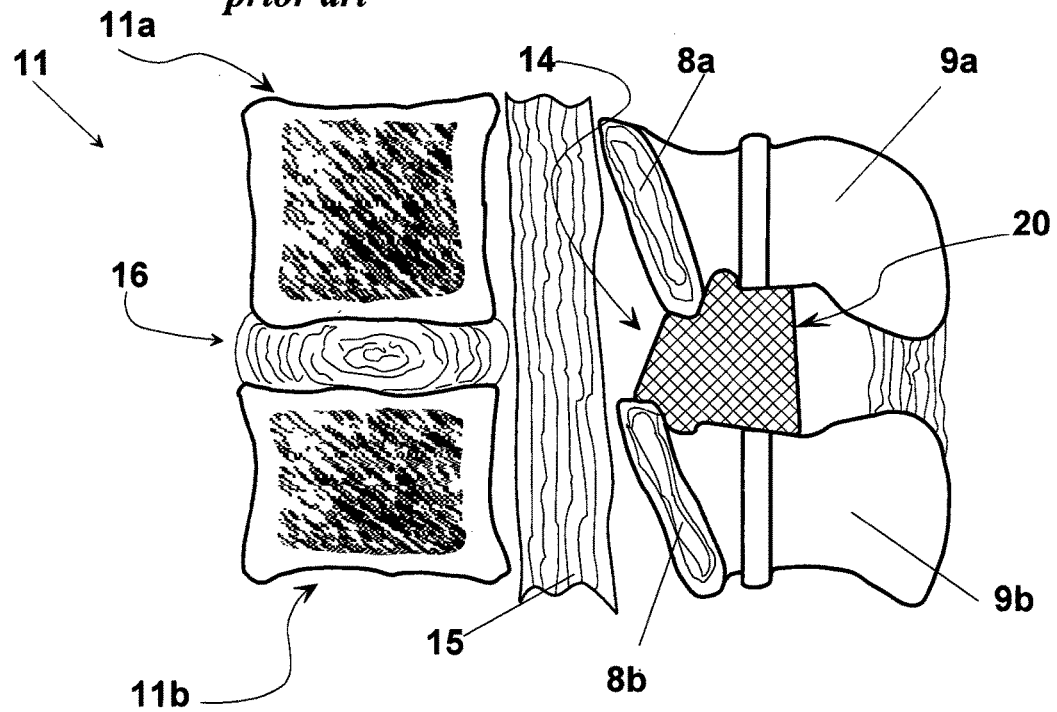
FIG. 2 is a perspective diagrammatical view of an implant of a prior art interlaminar intervertebral support.

With reference to FIG. 7 again, it is shown a longitudinal cross section of support element 30 that is implanted between adjacent vertebral bodies 13a and 13b. Annulus 17 of intervertebral disc 16 (FIGS. 2 and 3), which is arranged between adjacent vertebral bodies 13a and 13b, applies on support element 30 the forces that are directed outwards of the implant site, which tends to expel support element 30 from the implant site. As described above, protruding parts 37 of the medial upper and lower faces of support element 30 abut against inner surfaces 51a and 51b of the vertebral plates of vertebral bodies 13a and 13b. The protruding parts 37 resist these forces. Wing protruding parts 34 of lateral end portion 33 (FIG. 3) are arranged adjacent to the external surfaces 52a and 52b of vertebral bodies 13a and 13b. Support element 30 can be definitively or temporarily fastened, to external surfaces 52a and 52b. The fastening can be carried out by means of bone needles, i.e. of spikes 58, which are arranged within through holes 50.

Even if the diagrammatical view and the description of the implant of FIG. 7 has been depicted with reference to support element 30 of FIG. 4, this description also applies to the case of any support element according to the invention. In particular, this description applies to supporting elements 30', 40, 70, 70' of FIGS. 5, 14, 15, 17, respectively.

With reference to FIG. 19 support element 40 of FIG. 14 is shown, inserted between two vertebral bodies 13a and 13b of respective vertebrae 11a and 11b of spine 11 of a patient. Arrows 42 diagrammatically indicate the relative rotation between support halves 38a, 38b of device 40 about longitudinal axis 22 of support element 40. Rotation 42 is allowed by cylindrical element 41 arranged between support halves 38a, 38b.

With reference to FIG. 20, support element 70 of FIG. 15 is shown inserted between two vertebral bodies 13a and 13b of respective vertebrae 11a and 11b of spine 11 of a patient. Arrows 72 and 73 diagrammatically indicate the relative rotation between support halves 68a, 68b of device 70 about longitudinal axis 22 of support element 70 and about a transverse axis 22' of support element 70, respectively. Therefore, rotations 72, 73 of a ball joint are possible between support halves 68a, 68b. Rotations 72, 73 can be allowed by the convex and concave articulation surfaces 71' and 71" of support halves 68a, 68b, or they can be allowed by a spherical element 71 arranged between respective concavities 56 of inner faces 57a, 57b of support halves corresponding to support halves 68a and 68b. In this case, support halves 68a and 68b are cooperatively configured to receive a substantially spherical body.

With reference again to FIGS. 15 to 18, support element 70, 70' comprises a constraint means 67, 69 for constraining a first longitudinal portion 68b and a second longitudinal portion 68a. Constraint means 67, 69 serves for maintaining support element 70 in a spread-apart configuration, in which a distance $T_1$ between medial end 36 is shorter than a distance $T_2$ between lateral end 33 of first longitudinal portion 68b and of second longitudinal portion 68a (FIG. 15). In particular, constraint means 67, 69 comprise eyelets 67 integral to respective medial ends 36 of first longitudinal portion 68b and of second longitudinal portion 68a of support element 70. Eyelets 67 can engage with a breakable element 69. Breakable element 69 can be a low-strength surgical wire (FIG. 17), or a longitudinal pull-out element 69', for example a Kirschner wire (FIG. 15). In this case, a through hole 66 is provided through the convex surface of longitudinal element 68b, (FIGS. 17 and 18) for allowing a movement of Kirschner wire 69. Constraint means 67, 69, 69' allow maintaining support element 70 in the spread-apart configuration During the implant procedure, to assist introducing support element 70 between edge portions 53a, 53b of vertebral bodies 13a, 13b, as described hereinafter, more in detail.

As described above, in an exemplary embodiment, as shown in FIGS. 4 and 5, one or both proximal portions 33 of support element 30, 30' comprise respective holes 50. Holes 50 serve for housing respective fixation means that are adapted to anchor with external surfaces 52a, 52b of respective vertebral bodies 13a, 13b. Holes 50 are preferably made at positions that are symmetrical with respect to the middle plane of support element 30, 30'. The fixation means can be small bone needles, i.e. conventional spikes.

Even if holes 50 for housing fixation means have been described with reference only to examples 30, 30' according to an exemplary embodiment of the support element, they can be a part of any support element according to the invention. For example, holes 50 can be provided in the support elements 40, 70, 70' according to different exemplary embodiments and examples, as described.

Figure 6:
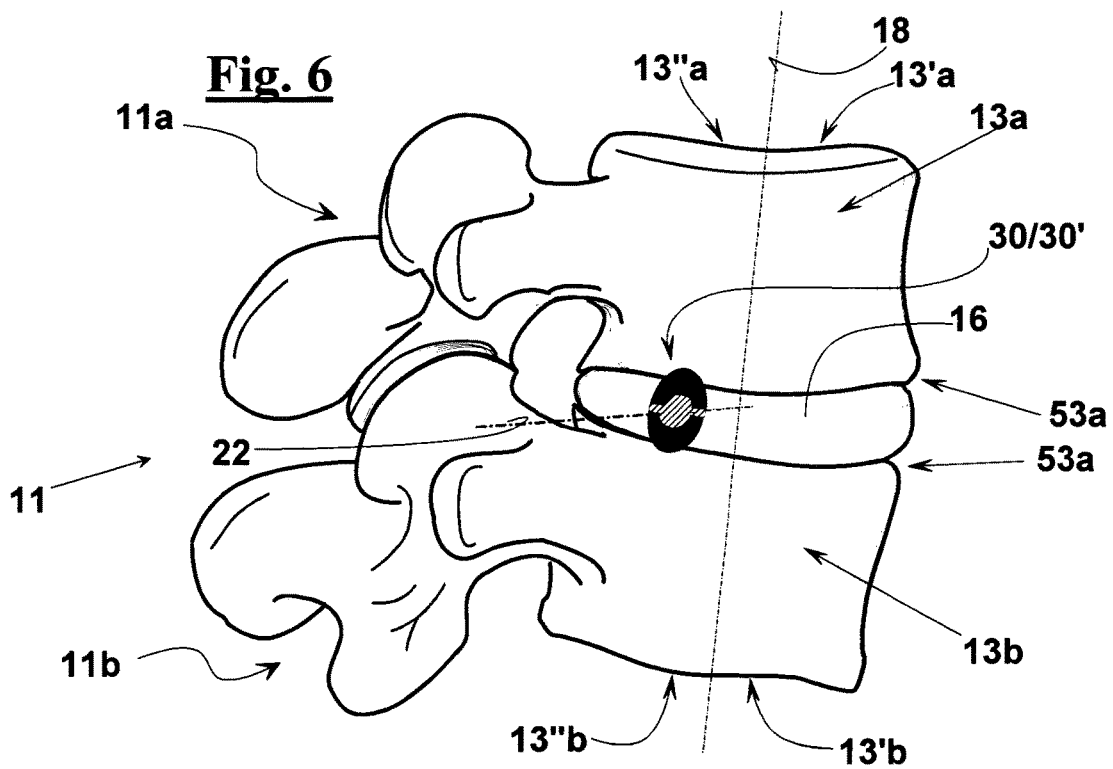
FIG. 6 is a perspective diagrammatical view of two adjacent vertebrae with a support element of FIG. 4 or of FIG. 5.
Figure 21:
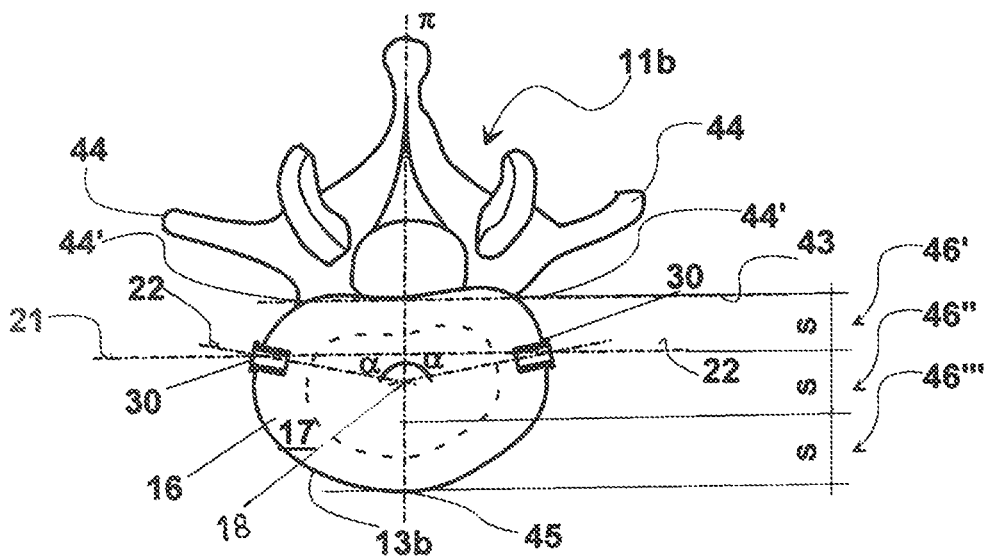
FIG. 21 is a cross sectional view of an implant comprising a couple of support elements according to the exemplary embodiments of FIGS. 4, 5, 14, 15 and 17.

With reference to FIGS. 6 and 21, a device is shown at a position of an implant, according to the invention, in a perspective view and in a cross sectional view, respectively. Such device comprises, for example support elements 30 (FIG. 4). Support elements 30 are inserted between edge portions 53a, 53b of vertebral bodies 13a and 13b, at rear halves 13"a, 13"b of vertebral bodies 13a, 13b. Longitudinal axes 22 of support elements 30 are at angles α with respect to a mid-sagittal plane π of the patient. Angles α are advantageously chosen in such a way that support elements 30 are located at the relative instantaneous rotation axis 21 between vertebrae 11a and 11b in the natural flexion-extension movement of the portion of a spine 11 which comprises vertebrae 11a and 11b. Angles α are normally set between 30° and 90°, in particular angles α are set between 45° and 75°.

Figure 3:
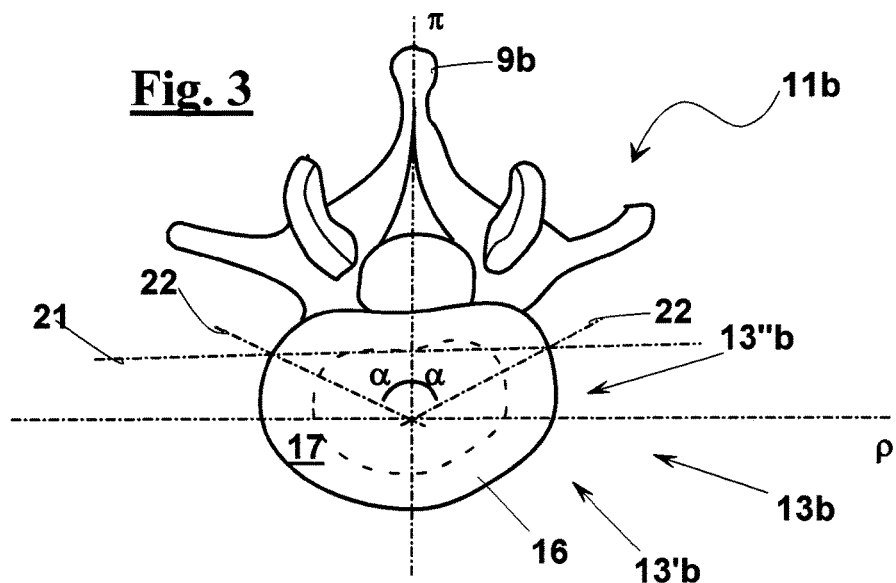
FIG. 3 is a top plan view of a vertebra, diagrammatically showing the position of the relative instantaneous rotation axis between a vertebra and an adjacent vertebra, with reference to the flexion-extension movement of the portion of spine that comprises the two vertebrae.

With reference to FIG. 3, by the expressions "front half of a vertebral body" and "rear half of a vertebral body" two portions 13'b, 13"b are meant where the vertebral body, for example vertebral body 13b, is ideally divided by a coronal plane ρ passing through a sagittal axis 18 of the vertebral body. In particular, rear half 13"b is the portion arranged on the same side of a spinous process 9b with respect to coronal plane ρ.

Still with reference to FIG. 21, the position of instantaneous rotation axis 21, and in any case the position of two support elements 30, is close to the limit between a rear third portion 46' and a medial third portion 46" of two adjacent vertebral bodies 13a and 13b.

By the expressions "rear third portion" 46' and "medial third portion" 46" two portions are meant of the three portions 46', 46", 46"' of the same height S that are located between:
 a line 43 ideally connecting the conjunction points 44' of pedicles 44 to vertebral body 13a, 13b and
 a front apex 45 of the vertebral body.

Even if the description of the support elements of the device of FIG. 21 has been made with reference to support element 30 (FIG. 4), this description applies to any support element according to the invention. For example, this description applies to supporting elements 30', 40, 70, 70' of FIGS. 5, 14, 15, 17, respectively.

Figure 23:
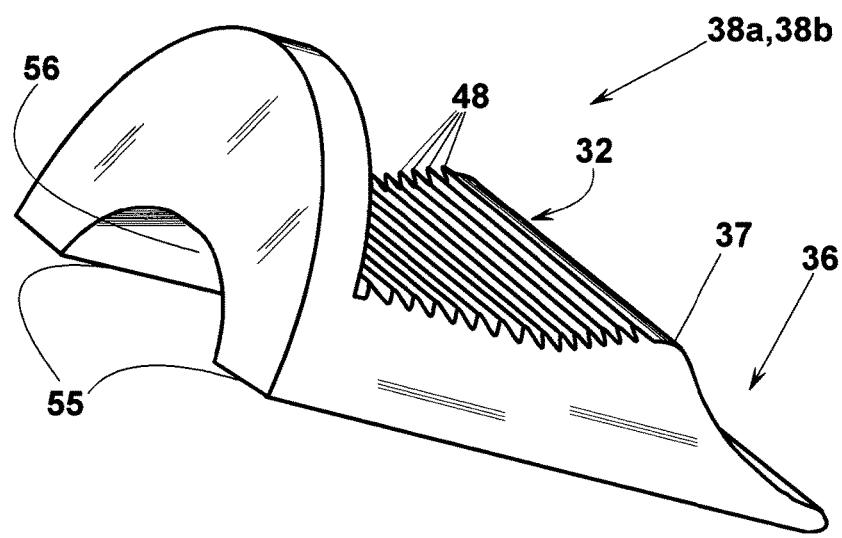
FIG. 23 shows an exemplary embodiment of a longitudinal portion of a support element.

With reference to FIG. 23, an exemplary embodiment of support halves 38a, 38b is shown, in which support surface 32 has a sawtooth profile 48. Sawtooth profile 48 serves for further stabilizing the position of support element 38a, 38b between edge portions 53a, 53b of vertebral bodies 13a, 13b.

Figure 24:
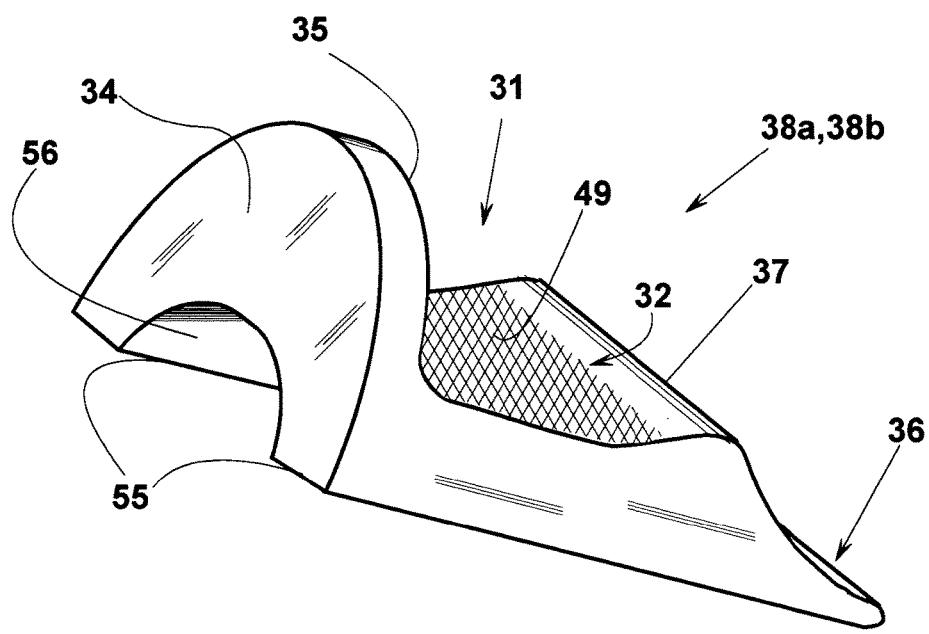
FIG. 24 shows an exemplary embodiment of a longitudinal portion of a support element.

With reference to FIG. 24, an exemplary embodiment of support halves 38a, 38b is shown. Support surface 32 of central elongated portion 31 is provided with an osteoinductive material 49, for example hydroxyapatite, silica or a functionalized osteoinductive material. Possibly, even rear face 35 of wing 34 and/or the surface of protruding part 37 of medial end portion 36 can expose an osteoinductive material.

Even if in FIGS. 23 and 24 support halves 38a, 38b are shown that are similar to support halves 38a, 38b of support element 30 (FIG. 4), sawtooth profile 48 and/or osteoinductive material 49 can be advantageously used in support halves 38a, 38b, 68a, 68b of support elements 30', 40, 70, 70' of FIGS. 5, 14, 15, 17, respectively.

An advantageous exemplary embodiment of the support elements according to the invention provides transversal grip elements, not depicted. To assist arranging each support element percutaneously, the gripping elements are preferably movable between a manoeuvre position and a surgical configuration. In the manoeuvre position the transversal gripping elements is located in the support element, whereas in the surgical configuration the transversal gripping elements protrude from the side surface of the support element and, in use, they engage stably with the fibres of annulus 17 of intervertebral disc 16.

With reference to FIGS. 25 and 26, a device 60 is described according to an exemplary embodiment of the invention, in which two support elements 30 are joined together by a mutual constraint element 61. Mutual constraint element 61 serves for preventing support elements 30 from moving with respect to each other. Therefore, once device 60 has been implanted in the intervertebral site, mutual constraint element 61 serves additionally for constraining support elements 30 to vertebral bodies 13a, 13b (FIG. 26). Constraint element 61 can be stiff or deformable in order to allow device 60 to match the intervertebral site between vertebral bodies 13a, 13b of a specific patient. In particular, constraint element 61 allows adjusting angles α to find the position of the instantaneous rotation axis, according to the above description.

The curved shape of constraint element 61 allows to put the device in its own intervertebral site following the path indicated by the arrow 62 of FIG. 26, remaining at a safe distance from the spinal channel, through a minimally invasive one-side percutaneous access, not shown. A device 60 comprising two support elements 30, 40 can be inserted after distracting the vertebral bodies 13a, 13b in order allow wings 34 to pass therethrough.

A perspective view of two adjacent vertebrae 13a, 13b is shown In FIG. 27, with a support element according to the exemplary embodiment of FIG. 25.

With reference to FIGS. 28, 29 and 30 an intervertebral support device 60' is described according to a further exemplary embodiment, in which two support elements 65', 65" are joined together by a mutual constraint element 63 for preventing support elements 65', 65" from moving with respect to each other. Each support element 65', 65" comprises an elongated portion 31', 31" to provide a support surface 32 for each adjacent vertebral body 13a, 13b, as FIG. 30 shows. Support element 65" has protruding parts 34 which protrudes with respect to support surface 32, such as the wings of support elements 30, 30', 40'70, 70', whereas the support element 65' is not provided therewith. Furthermore, each support element 65', 65" comprises a couple of longitudinal support halves 68a, 68b and an interface means by which the relative position of support halves 68a, 68b can be changed to some extent, and therefore a support surfaces 32 of each support element 65', 65" can be moved with respect to each other. Only the interface means of support element 65" in shown in the view of FIG. 28. In the device of FIG. 28 the interface means comprises articulation surfaces 71', 56 between support halves 68a, 68b as described above with reference to FIGS. 15 and 16. However, the interface means can also comprise a central bearing portion such as bearing 39 of FIG. 4, a cylindrical element as the cylindrical element such as cylindrical element 41 of FIG. 14, or a substantially spherical or ellipsoidal one, which is housed between two concave surfaces of inner faces 57a, 57b, which can be represented as in FIG. 28 as well. Mutual constraint element 63 comprises an upper portion 63a and a lower portion 63b that ideally connect protruding portions such as protruding portions 37 of support element 30 of FIG. 4, which abut against respective inner surfaces 51a, 51b of adjacent vertebral bodies 13a, 13b, as shown in FIG. 30. Upper and lower portions 63a, 63b of constraint element 63 can comprise resilient parts or shape-memory parts that are adapted to remain in contact with the vertebral plates of vertebral bodies 13a, 13b along their own extensions. Device 60' is well-suited for a minimally invasive implant inserted through an one-side access. The structure of support element 65', where one of the two support elements is not provided with protruding parts such as wings 34, assists implanting the device between adjacent vertebral bodies 13a, 13b, and limits or eliminates the need of a preliminary vertebral distraction.

Mutual constraint element 63 can be made of titanium, or of tantalum. Mutual constraint element 63 can also be made of a titanium alloy and/or of a tantalum alloy.

With reference to FIGS. 31A and 31B, a working surgical cannula 80 is described for implanting a device according to the invention. The surgical cannula 80 has a substantially elliptical cross section and is adapted to slidingly receive a support element according to the invention, for example one of the support elements shown in FIGS. 4, 5, 14, 15, 17. The working surgical cannula 80 has a manoeuvre end portion 81 and a positioning end portion 82 to be positioned at the surgical site access. The positioning end portion 82 has a side tang extension 83 that is configured to be inserted between edge portions 53a, 53b of adjacent vertebral bodies 13a, 13b. The width W of side tang extension 83 is enough to create a predetermined distraction between adjacent vertebral bodies 13a, 13b at the surgical site, and to push working surgical cannula 80 against adjacent vertebral bodies 13a, 13b. In the example shown, tang extension 83 occupies a position at the minor axis 85 of the substantially elliptical cross section of cannula 80.

In the exemplary embodiment of FIG. 31A, tang portion 83 of working surgical cannula 80 has rounded end edges 84, to prevent the edge portions of vertebral bodies 13a, 13b from being abraded when tang portion 83 is inserted between vertebral bodies 13a, 13b. For the same reason, working surgical cannula 80 can be made of a plastic material.

Figure 22:
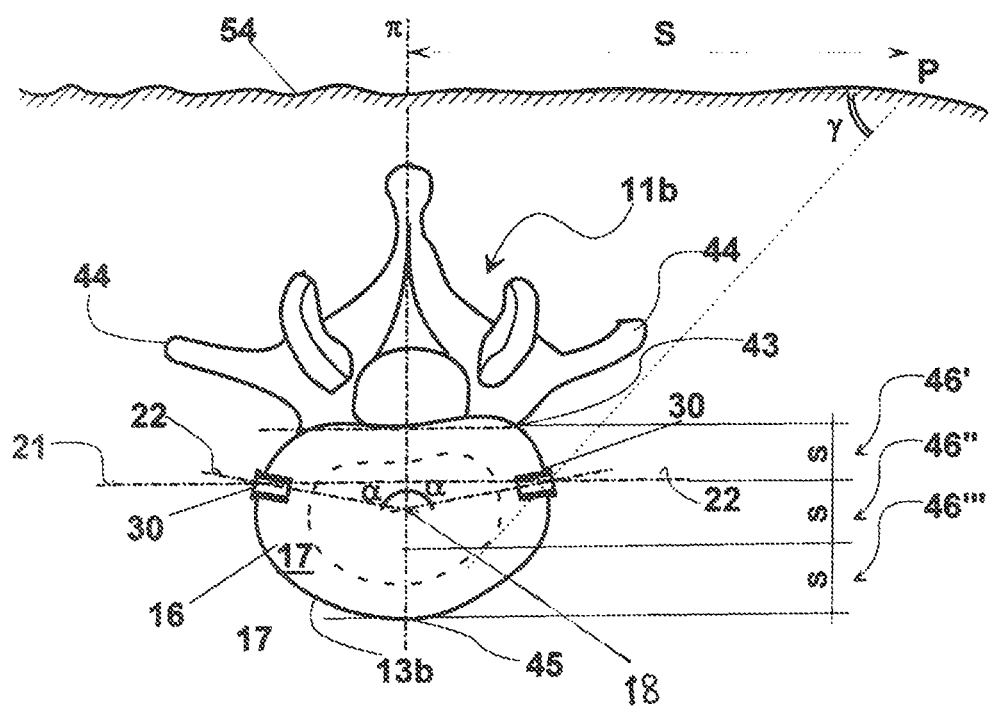
FIG. 22 is a cross sectional view as shown in FIG. 21, and of the skin of the back of the patient, showing a possible access point to reach the intervertebral site.

With reference to FIGS. 22, 32A and 32B, a method is described for implanting a vertebral support device 30 into a surgical implant site between rear halves 13"a, 13"b of adjacent vertebral bodies 13a, 13b. The method can provide creating two opposite side openings in the skin 54 of the patient, at a level that corresponds to the intervertebral level between two adjacent vertebral bodies 13a, 13b. The implant is performed under scopic control. As shown in FIG. 32A, a guide wire 74, typically a Kirschner wire, is brought at the intervertebral space of two adjacent vertebral bodies 13a, 13b. Then, a first surgical cannula 75 is inserted on guide wire 74, until it reaches the intervertebral space access, at the surgical implant site. In a subsequent step, a plurality of surgical cannulas 75', 75'', 75''' of increasing diameter are concentrically inserted about one another. In particular, three concentric cannulas are shown. The diameter of last cannula 75''' is long substantially as the distance between the edge portions of adjacent intervertebral bodies 13a, 13b. At last, a working cannula 80 is concentrically inserted on last cannula 75'''. The size of working cannula 80 is slightly larger than the diameter of last cannula 75'''. In particular, working cannula 80 is the same type as shown in FIGS. 31A and 31B. As shown in FIG. 32B, tang extension 83 of working cannula 80 is inserted between the edge portions of vertebral bodies 13a, 13b. This way, tang extension 83 causes a slight distraction of vertebral bodies 13a, 13b with respect to each other. Such distraction is mated to an extension enough for assisting the introduction of support element 30 between vertebral bodies 13a, 13b. Once working cannula 80 has been secured between the edge portions of vertebral bodies 13a and 13b, guide wire 74 and surgical cannulas 75', 75'', 75''' are withdrawn. Then, support element 30 is inserted into working surgical cannula 80, until it reaches the intervertebral space access. Support element 30 is followed by an elongated element of compression or beater 90 through cannula 80. Once achieved access to the surgical implant site, a final compression force is applied on support element 30 by means of beater 90 to secure support element 30 within the surgical implant site. Finally, beater 90 and working surgical cannula 80 are withdrawn from patient's body.

With reference to FIGS. 33 and 34, a method is described for implanting a device that comprises a support element such as support element 70 of FIG. 15, which can have a longitudinally spread-apart configuration, as also shown in FIG. 15. In the spread-apart configuration, distance $T_1$ between medial ends 36 is shorter than distance $T_2$ between lateral ends 33 of longitudinal portions 68a and 68b. Support element 70 is maintained in the spread-apart position by previously described constraint means 67, 69'. This constraint means is advantageously prearranged before inserting support element 70 into working cannula 80. After reaching the access to the surgical implant site between edge portions 53a and 53b of vertebral bodies 13a and 13b, constraint means 67, 69' are removed. This way, support element 70 is allowed to leave the spread-apart configuration of FIG. 15. In the case of support element 70, the removal of the constraint means is carried out by withdrawing a Kirschner wire 69' from the couple of mutual engagement eyelets 67 of two longitudinal elements 68a, 68b. Kirschner wire 69' is inserted into the working cannula along with support element 70, through a longitudinal through hole 93 made inside beater 90. Beater 90 has a clamping means 91 that is configured to engage with respective housings 77 of lateral end 33 of support element 70, for maintaining this support element in the spread-apart configuration. By releasing clamping means 91 from housings 77, and maintaining a central body 92 of beater 90 pressed upon housing 76 of support element 70, support element 70 is caused to be closed within the surgical implant site. Support surfaces 32 and medial end 36 are inserted between edge portions 53a and 53b of vertebral bodies 13a and 13b.

In case of device 70', the removal of the constraint means is carried out by breaking a thin surgical wire 69 that engages eyelets 67 and maintains medial end 36 of the two elements longitudinal joined to each other. This can be made by impulsively pushing beater 90 against support element 70'. Otherwise, the surgical wire can be broken by withdrawing the gripping means that are slidingly arranged within through longitudinal holes 93 and 66 of beater 90 and of convex portion 71' of support element 70', respectively. Support device 70' has a couple of diametrically opposite V-passages 78 for moving a clamping means, not shown, which is configured to engage with a rear portion of wings 34.

Obviously, the engaging location of the clamping means can be like housing 77 or like V-passages 78 independently from the type of constraint means between longitudinal portions 68a and 68b, which are adapted to keep two longitudinal portions 68a and 68b in the spread-apart configuration.

In case of devices 60, 60' of FIGS. 25, 28 an implant procedure is preferable that provides making only one opening, i.e. an one-way access to the intervertebral surgical implant site. The curved shape of constraint element 61 allows to put the device into its own intervertebral site following the path indicated by arrow 62 of FIG. 26, using a conventional guide means or in the way described above in the case of a bilateral approach.

In FIGS. 3, 6, 19, 20, 21, 22, 26, 27, 32A/B the shape of the lumbar vertebrae can be recognised. In any case, this is not intended to limit the application extent of the device according to the invention. In fact, if a suitable size is chosen, the device according to the invention can be used between two adjacent vertebrae at any level of a spinal column.

The foregoing description of specific exemplary embodiments of the device according to the invention, for application of an intervertebral support device, and of its mode of use, will so fully reveal the invention according to the conceptual point of view so that other, using the prior art, will be able to modify and/or to adapt for various applications these specific exemplary embodiments without further researches and without parting from the inventive concept, and it is therefore to be understood that such adaptation and changes will have to be considered ad as equivalent of the specific exemplary embodiments. The means and the material to provide the various functions described herein could have a different nature without, for this reason, departing from the scope of the invention. It is to be understood that the expressions or the terminology used that is employed herein is for the purpose of description and not of limitation.

The invention claimed is:

1. An intervertebral support device configured to be arranged between two adjacent vertebral bodies of the spine of a patient in such a way that a relative movement is allowed between said adjacent vertebral bodies and that said support device can contribute to bear the load of an upper vertebral body on a lower vertebral body, said vertebral bodies having a sagittal axis and a mid-sagittal plane, said adjacent vertebral bodies having a respective front half, a respective rear half, and respective edge portions that face each other, said device comprising a pair of support elements, each support element of said pair having two support halves, and at least one support surface, said support elements configured to be inserted between said edge portions of said respective rear half of said adjacent vertebral bodies, and dorsally with respect to said sagittal axis, such that said support surface engages with said edge portions, and assists to bear said load, said support elements configured to be arranged in juxtaposition, and on a same horizontal plane between said adjacent vertebral bodies, and said support elements configured to be arranged at opposite sides of said edge portions with respect to said mid-sagittal plane, at respective angles centered on said sagittal axis, and measured starting from said mid-sagittal plane, said respective angles set between 30° and 90°, wherein each support element comprises:

a first longitudinal portion and a second longitudinal portion, which provide both a support surface portion for said edge portions of said upper and lower adjacent vertebral bodies, respectively, said support surface portion of said first longitudinal portion and said support surface portion of said second longitudinal portion having a predetermined relative position;

an interface means between said first longitudinal portion and said second longitudinal portion by which a mobility of said relative portion is left, such that a plurality of use relative positions are allowed according to a shape of said spine corresponding to a position and/or to a movement of said patient, in order to maintain a predetermined anatomic distance between said adjacent vertebral bodies;

wherein said interface means comprises an element having a convex surface arranged between said first longitudinal portion and said second longitudinal portion, said element having a convex surface configured to engage with respective inner concave surfaces of said first longitudinal portion, and of said second longitudinal portion, and configured to allow a relative rotation of said first longitudinal portion, and of said second longitudinal portion with respect to each other; and wherein said element having a convex surface is an ellipsoidal element, configured to allow said relative rotation that can be obtained as a combination of a rotation about a substantially longitudinal axis and of a rotation about a transverse axis of said intervertebral support device.

2. The device according to claim 1, wherein said support elements are configured to be arranged at opposite sides of said edge portions with respect to said mid-sagittal plane, at said respective angles, such that each support surface is arranged at the instantaneous rotation axis of the natural relative flexion-extension movement of the vertebra comprising said adjacent vertebral bodies.

3. An intervertebral support device according to claim 1, wherein said angles (α) are set between 45° and 75°.

4. The device according to claim 1, wherein said support element comprises a constraint means which constrains said support element to a vertebral body of said adjacent vertebral bodies, wherein said constraint means comprises a protruding part of said support element that protrudes with respect to said support surface, said protruding part configured to abut against an inner surface of an edge portion of a vertebral body of said vertebral bodies, and/or against an outer surface of said vertebral body.

5. The device according to claim 4, wherein said protruding part comprises a flange, or a pair of wings, that extend in a substantially perpendicular way with respect to said support surface at opposite sides with respect to said support surface.

6. The intervertebral support device according to claim 5, wherein at least said flange or at least one of said wings comprises a through hole that is configured to receive a bone nail for fastening said support element to said vertebral body.

7. The intervertebral support device according to claim 5, wherein only one of said support elements has said pair of wings, such that said intervertebral support device is configured to be inserted between said vertebral bodies without any substantial distraction of said vertebral bodies.

8. The device according to claim 1, wherein said interface means comprises a convex portion of a surface, which is internal to said support element, of said first or of said second longitudinal portion, and a concave portion of an inner surface respectively of said first or of said second longitudinal portion, said concave portion and said convex portion arranged to movably engage with each other, such that a relative rotation is allowed of said first longitudinal portion and of said second longitudinal portion with respect to each other.

9. The intervertebral support device according to claim 8, wherein said convex portion and said concave surface/s is/are ellipsoidal surface/s, wherein said convex portion has a curvature radius that is shorter than a curvature radius of said concave portion, or of one of said concave surfaces.

10. The device according to claim 1, wherein said support element comprises a constraint means between said first longitudinal portion and said second longitudinal portion to maintain said support element in a spread-apart configuration, wherein first end portions of said first, and of said second longitudinal portion, which face each other, are at a distance that is shorter than a distance between second end portions, which face each other, of said first longitudinal portion, and of said second longitudinal portion, said second end portions opposite to said first end portions of respective longitudinal portions, to assist introducing said support element between said edge portions of said adjacent vertebral bodies.

11. The device according to claim 1, wherein said support element has a size selected from the group consisting of:
an overall length set between 8 and 18 mm;
a height, measured between said support surfaces, set between 4 and 12 mm.

12. The device according to claim 1, wherein the overall length is set between 10 and 15 mm.

13. The device according to claim 12, wherein the overall length is about 12 mm.

14. The device according to claim 12, wherein the height is set between 8 and 10 mm.

15. The device according to claim 12, wherein the overall length is about 12 mm.

16. The device according to claim 1, wherein the ellipsoidal element is a spherical element.

17. The intervertebral support device according to claim 1, wherein said support element comprises a constraint means which constrains said support element to a vertebral body of said adjacent vertebral bodies, wherein said constraint means is configured to create an adhesion of said support surface with said edge portion of one of said adjacent vertebral bodies, wherein said constraint means is selected from the group consisting of:

a friction engagement means between said support surface and said edge portion of said adjacent vertebral bodies; and an osteoinductive material exposed by said support surface.

18. The intervertebral support device according to claim 1, comprising a mutual constraint means between said support elements of said pair of support elements, said mutual constraint means arranged in use in a region located between said adjacent vertebral bodies.

19. The intervertebral support device according to claim 18, wherein the mutual constraint means comprises a first constraint portion and a second constraint portion, said first constraint portion and said second constraint portions configured to abut against the vertebral plates of said vertebral bodies.

20. The intervertebral support device according to claim 19, wherein said first and said second constraint portions comprise resilient parts, or parts, that are made of a shape-memory material.

21. The device according to claim 18, wherein said mutual constraint means comprises a substantially stiff element that is integral to said support elements.

22. The device according to claim 18, wherein said mutual constraint means comprises a surgical wire.

23. The device according to claim 18, wherein said mutual constraint means can be dismantled from at least one of said support elements.

24. The device according to claim 18, wherein said mutual constraint means comprises a position adjustment means for adjusting the position of at least one support element of said pair of support elements with respect to said edge portions of said adjacent vertebral bodies and/or for adjusting the distance of a support element with respect to the other support element of said pair of support elements.

* * * * *